United States Patent [19]
Gluzman et al.

[11] Patent Number: 5,852,015
[45] Date of Patent: Dec. 22, 1998

[54] TRIAZINE CONTAINING ANIONIC COMPOUNDS USEFUL AS ANTIVIRAL AGENTS

[75] Inventors: Yakov Gluzman, deceased, late of Upper Saddle River, N.J., by Ilan Gluzman, executor; James P. LaRocque, Highland Mills, N.Y.; Bryan M. O'Hara, Pearl River, N.Y.; John E. Morin, Cold Spring, N.Y.; George A. Ellestad, Pearl River, N.Y.; Boris Mitsner, Nanuet, N.Y.; Wei-Dong Ding, Nanuet, N.Y.; Yuri E. Raifeld; Antonina A. Nikitenko, both of Tarrytown, N.Y.

[73] Assignee: American Cyanamid Company, Madison, N.J.

[21] Appl. No.: 789,038

[22] Filed: Jan. 27, 1997

Related U.S. Application Data

[60] Provisional application No. 60/011,542 Feb. 13, 1996.

[51] Int. Cl.$^6$ .......... C07D 403/10; A61K 31/53
[52] U.S. Cl. .......... 514/245; 540/598; 544/193.2; 544/219; 544/212; 544/209; 544/198; 514/241; 514/212
[58] Field of Search .......... 544/193.2, 219, 544/212, 209, 198; 514/241, 245, 212; 540/598

[56] References Cited

U.S. PATENT DOCUMENTS

| | | | |
|---|---|---|---|
| 5,359,131 | 10/1994 | Cardin et al. | 562/51 |
| 5,429,767 | 7/1995 | Zelger | 252/174.17 |

OTHER PUBLICATIONS

Huang–Minlon, "The Reaction of Hydrazine Hydrate on Nitro–Compounds and a New Route to Synthetic Oestrogens," J. Am. Chem. Soc., 70, 2802 (1948).

*Primary Examiner*—John M. Ford
*Attorney, Agent, or Firm*—Steven R. Eck

[57] ABSTRACT

This invention provides triazine ring containing anionic compounds, pharmaceutical compositions containing these compounds and methods utilizing these compounds for treating viral infections, particularly infections by respiratory syncitial virus, the compounds having the general structure:

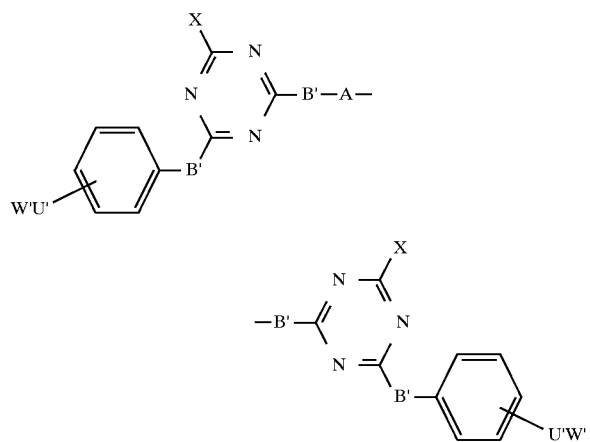

and the pharmaceutically acceptable salt thereof.

39 Claims, No Drawings

TRIAZINE CONTAINING ANIONIC COMPOUNDS USEFUL AS ANTIVIRAL AGENTS

This application claims the benefit of U.S. application Ser. No. 60/011,542, filed Feb. 13, 1996 and is a continuation-in-part of that prior application.

This invention relates to new triazine ring containing anionic compounds which are useful in treating viral infections and in particular human respiratory syncytial virus [HRSV]. This invention also relates to methods of treating viral infections and pharmaceutical compositions therefore.

BACKGROUND OF THE INVENTION

Human respiratory syncytial virus[HRSV] was first discovered in 1956 and is worldwide in distribution. It is an important cause of upper and lower respiratory tract disease causing illness in infants and young children resulting in approximately 100,000 hospitalizations and 5,000 deaths yearly in the United States (Chanock, R. M., Kim, H. K., Brandt, C. D., and Parrott, R. H. 1982. Respiratory syncytial virus, pp 471–489, in Viral Infections of Humans, Second Edition, A. S. Evans, editor (Plenum Press, NY). Glezen, W. P., Taber, L. H., Frank, A. L., and Kasel, J. A., 1986. Risk of primary infection and reinfection with respiratory syncytial virus. Am. J. Dis. Chil. 140;543–546. MacDonald, N. E., Hall, C. B., Suffin, S. C., Alexson, C., Harris, P. J., and Manning J. A. 1982. Respiratory syncytial virus infection in infants with congenital heart disease. New England Journal of Medicine 307;397–400.

About 30 percent of hospitalized young children with acute respiratory disease have respiratory syncytial virus infection. In older children and adults the disease is milder. HRSV appears to also be a major cause (equivalent to influenza) of morbidity and mortality in the elderly. (Fleming, D. M. and Cross, K. W. 1993. *Respiratory syncytial virus or influenza?* Lancet 342;1507–1510.). Infections with respiratory syncytial virus are referable to all segments of the respiratory tract, are usually associated with fever, cough, runny nose, and fatigue, and are diagnosed clinically as bronchitis, bronchiolitis, pneumonia, croup, or viral infection. In older children and adults the virus is generally limited to replication in the upper respiratory tract. Infants may be more severely involved when the virus extends into the lungs. Lung damage can be permanent.

Primary infection with respiratory syncytial virus occurs early in life, usually before 4 years of age. Among children, illness caused by this virus tends to occur at least once each year in rather sharply defined outbreaks of several months duration. Epidemics are sharply circumscribed, generally for 3 to 5 months. In family studies, children in early school years frequently introduce the virus into the home, infecting younger members of the family more severely than other family members. The clinical consequence of infection is most severe on first experience and becomes milder in older individuals who are immunologically experienced.

The effects of respiratory syncytial virus can range from unapparent infection to severe pneumonia and death. Inflammation of the respiratory track is responsible for most symptoms. Complete recovery in most cases occurs in one to three weeks with the production of antibody which appears to persist throughout life. In the United States about 30 percent of one year old infants and 95 percent of five year old children have circulating respiratory syncytial virus antibody. Reinfection in older infants, children, and adults with antibody gives mostly mild upper respiratory illnesses in the form of colds. In infants and young children, the infection is treated with ribavirin, a broad-spectrum antiviral. Use of this compound is severely limited by toxicity. There is therefore a great need for a new therapeutic agent for the treatment of HRSV infection.

U.S. Pat. No. 5,359,131 teaches sulfonic acid stilbenes which block the infection of cells by herpes simplex virus (HSV), human immunodeficiency virus (HIV) and cytomegalovirus (CMV).

The present invention relates to novel triazine ring anionic compounds which exhibit antiviral activity and in particular human respiratory syncytial virus[HRSV] activity.

This invention relates to new compounds selected from those of the general Formula I:

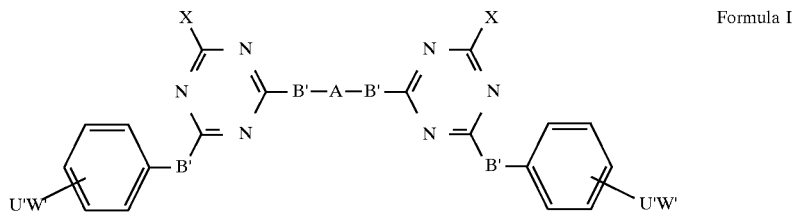

Formula I wherein:

A is a moiety selected from the group consisting of

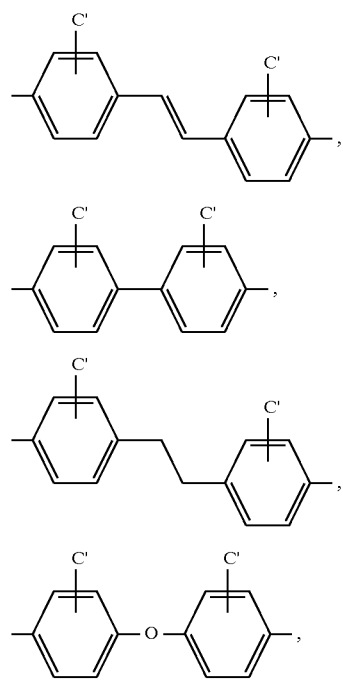

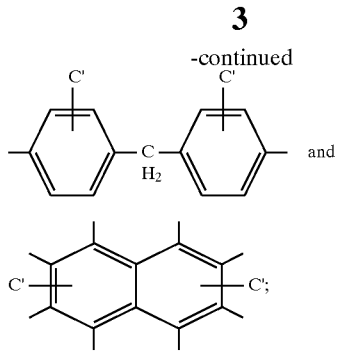

C' is selected from —SO$_3$H, —OSO$_3$H, —OH, or —COOH;

B' is —NH, NR$^1$ or O;

R$^1$ is selected from H, (C$_1$–C$_6$)lower alkyl, straight or branched, wherein the carbon atoms may be optionally substituted with Cl, Br, F, OH or CN;

X is Cl, F, or the moiety

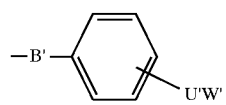

U' is selected from the group of —SO$_2$, —CO, —NC(O), or —NC(S);

W' is selected from the moieties:

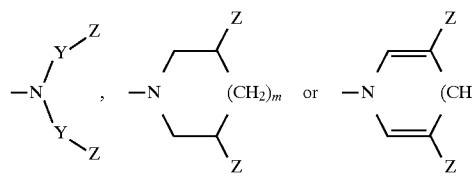

Y is —(CH$_2$)$_n$—;

n is 0 to 6;

m is 0 to 2;

Z is selected from H, CH$_3$, CF$_3$, —CH$_2$—(halogen), where halogen is Cl, Br, F or I, —CH$_2$OH, —COOH, —COO (C$_1$–C$_6$)lower alkyl straight or branched, —CONR$^2$R$^2$, CN or

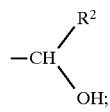

R$^2$, in each occurrence, is independently selected from H or (C$_1$–C$_6$)lower alkyl;

and the pharmaceutically acceptable salts and esters thereof.

It is understood that, in cases where m is 0, five-membered rings would be indicated for W'.

The pharmaceutical acceptable salts of the compounds of this invention are those whose cations that are not substantially toxic at the dosage administered to achieve the desired effect and do not independently possess significant pharmacological activity. Illustratively, these salts include those of alkali metals, for example, Na or K; alkaline earth metals, such as Ca or Mg; light metals of group IIIa including Al; and organic primary, secondary and tertiary amines or ammonia. Sodium salts are preferred.

DETAILED DESCRIPTION OF THE INVENTION

Within the group of compounds defined by Formula I, certain subgroups of compounds are broadly preferred. Broadly preferred are those compounds, or a pharmaceutically acceptable salt thereof, wherein A is

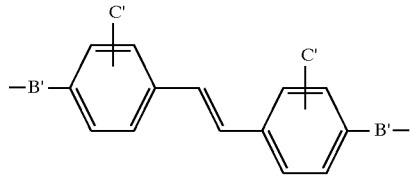

Especially preferred is the compound wherein

C'=—SO$_3$H, B'=—NH, Y=—CH$_2$—, Z=—CH$_2$OH

Most preferred is the compound wherein

C'=—SO$_3$H, B'=—NH, Y=—CH$_2$CH$_2$—, Z=—CONH$_2$

Most highly preferred is the compound wherein A is

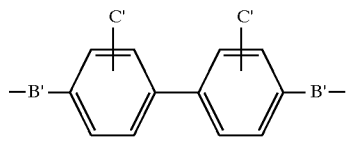

and C'=—SO$_3$H, B=—NH, Y=—CH$_2$CH$_2$—, Z=—CONH$_2$

The novel compounds of the present invention may be prepared according to the following schemes. Referring to Scheme I, condensation 2 where A and B' are hereinbefore defined with triazines having the structure 3 where X is Cl, F or Br at about 0° C. and pH from about 6.5 to about 7.2 gives intermediates 4. Further reaction of the compounds of the Formula 4 with compounds of formula 5 wherein U', B' and W' are hereinbefore defined at a temperature of from about 45° C. to about 55° C. and pH 6.5–7.2 followed by heating at 100°–120° C. at pH 6.5–7.2 gives the desired products of Formula I, above, which is referred to in the schemes below as 1.

Scheme I

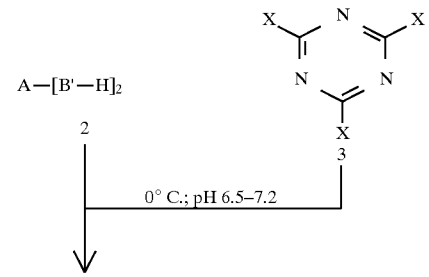

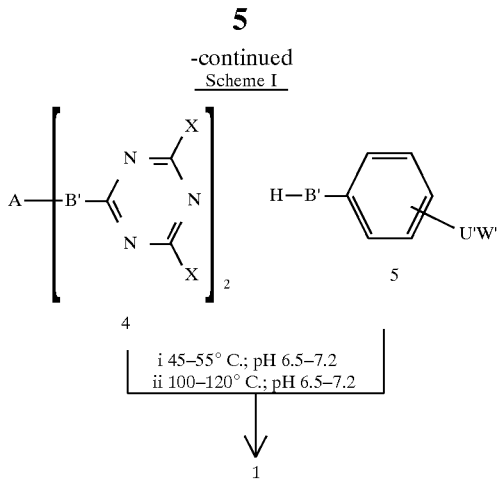

In an alternate route to the compounds of Formula I, as shown in Scheme II, reaction of triazine 3 where X is Cl, Br or F with compounds 5, where B' and W' are hereinbefore defined at from about −5° to about 5° C. and pH 6.5–7.2 gives condensation products 6. Reaction of 6 where B', and W' are hereinbefore defined and X is Cl, Br or F and 2 where A and B' are hereinbefore defined at from about 45° C. to about 55° C. and pH from about 6.5 to about 7.2 followed by heating at from about 100° C. to about 120° C. and pH 6.5–7.2 gives 1.

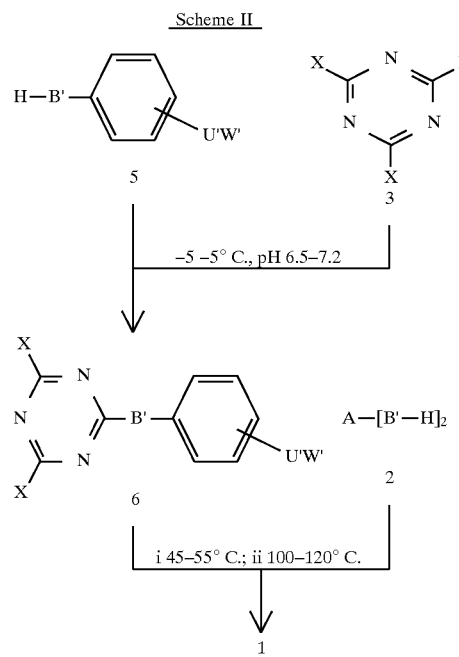

The stepwise condensation of the starting compounds 2, as shown in Scheme I, and 5 as shown in Scheme II, with triazines 3 where X is Cl, Br or F are reacted similarly in aqueous or organic-aqueous media in the presence of suitable bases such as sodium or potassium hydroxides, carbonates, phosphates or bicarbonates. Phosphate buffer at pH 7.0 is preferred.

The first step of condensation is carried out in pH ranges from about 4 to about 8, preferably at a pH of from about 6.5 to about 7.2 and at temperatures from about −10° to about 30° C., preferably from about −5° to about 5° C. The exchange of the second halogen atom of the triazine derivatives is effected in the same pH range and from about 10° to about 70° C., preferably at a temperature of from about 45° to about 55° C. The exchange of the third halogen atom of the triazine derivatives is effected in the same pH range and at temperatures from about 80° C. to about 150° C., preferably from 100° to 120° C.

The exchange of the second or the third halogen atoms of the triazine derivatives of the Formula 6 (Scheme II) is effected also in organic media in the presence of organic bases, such as trialkylamines, including triethylamine, diisopropylethylamine, or N-(lower)alkylpiperidine.

Starting materials for use in the general synthetic procedures outlined in Schemes I and II are commercially available or can be synthesized according to H. Adkins, E. F. Steinbring, E. Pickering. J. Amer. Chem. Soc., v. 46, p. 1917 (1924), G.B. Pat. No. 1,194,388 (Jun. 10, 1970) and U.S. Pat. No 5,359,131 (Oct. 25, 1994). The starting compounds of Formula 2 wherein B' is oxygen can be prepared from the substituted compound of Formula 2 (B'=—NH₂) as shown in Scheme III.

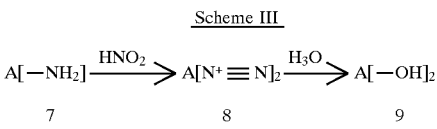

Primary aromatic amines 7 where A defined previously are reacted with nitrous acid or with other chemical reagents (for example, organic ester of nitrous acid) for diazotization of the primary amine to yield diazonium salts 8 that are hydrolyzed to compounds of Formula 9 containing phenolic groups.

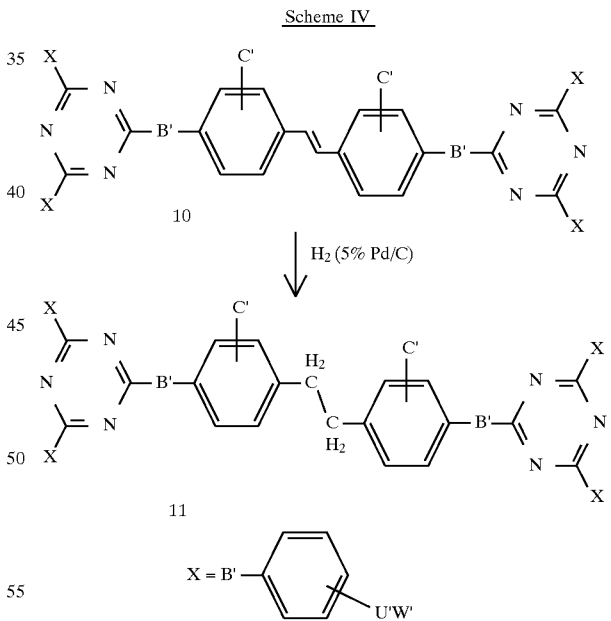

Referring to Scheme IV, the compounds (10) of stilbene series can be transformed to the compounds (11) of bibenzyl series by catalytic reduction conditions (hydrogen—Pd/C) or by related reduction conditions known in the art for converting substituted stilbene compounds into bibenzyl compounds [Huang-Minlon, *J.Amer.Chem.Soc.* (1948) 70 2802].

The compounds (12 and 13) of the Formula 1 with Z=—COOH can be prepared by basic hydrolysis to the compounds (14) in the pH ranges from 7.5 to 10.0, preferably 8.0–8.5 and from 80° to 150° C., preferably 100° to 120° C. (Scheme V):

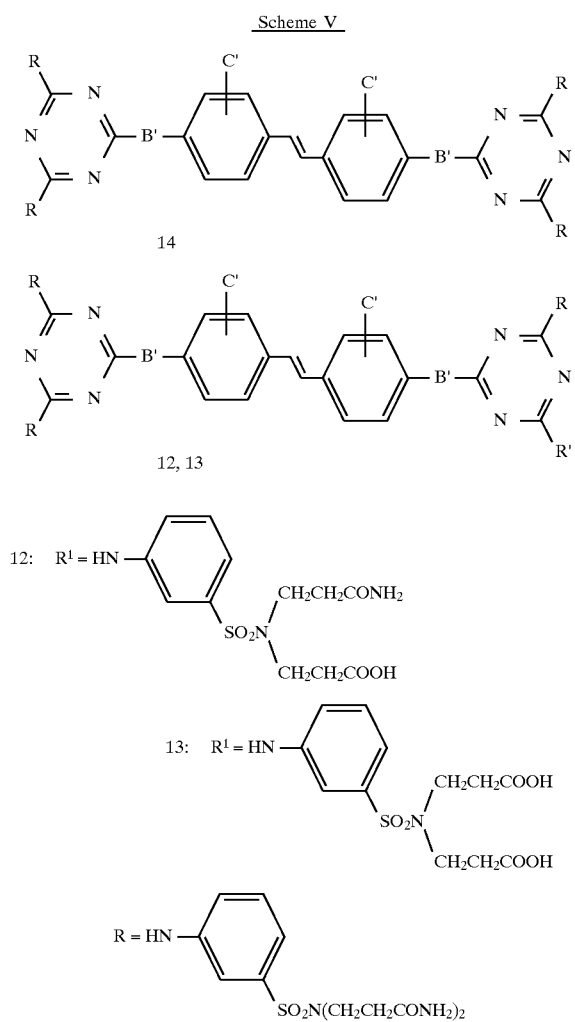

m-Aminobenzamides 17, where U' is —SO2 or —CO, Y and Z are hereinbefore defined, are synthesized according to the Scheme VI.

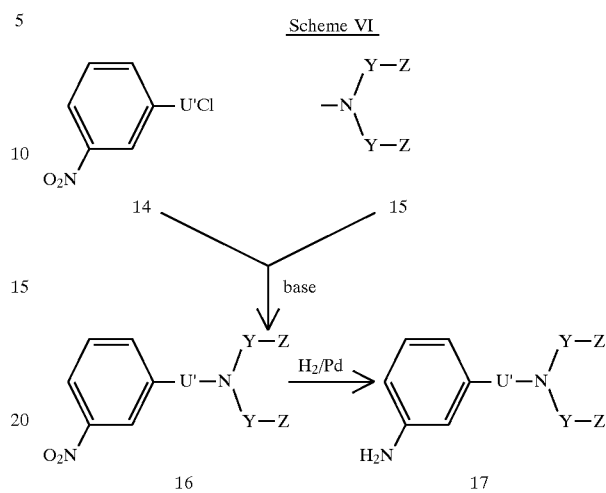

Imides 15 are transformed into m-nitrosulfonates 16, using a suitable variant of the amidation or tosylation methods (T. W. Greene, P. G. M. Wuts, Protective Groups in Organic Chemistry, John Wiley & Sons, New York 1991, pp. 349–379). The nitro-compounds 16 are then reduced to the amino-compounds 17 by catalytic hydrogenation (hydrogen—Pd/C).

Piperazine derivatives 21,22, where Z is —COOH or —CONH$_2$, are synthesized according to the Scheme VII from 3,5-piperidinedicarboxylic acid 18. Reduction of the aromatic ring and m-nitrotosylation of the piperidine derivative 19 leads to the compound 20, which is either reduced to a carboxyl containing compound 21 or converted into a carbamoyl containing compound 22 by esterification and ammonolysis.

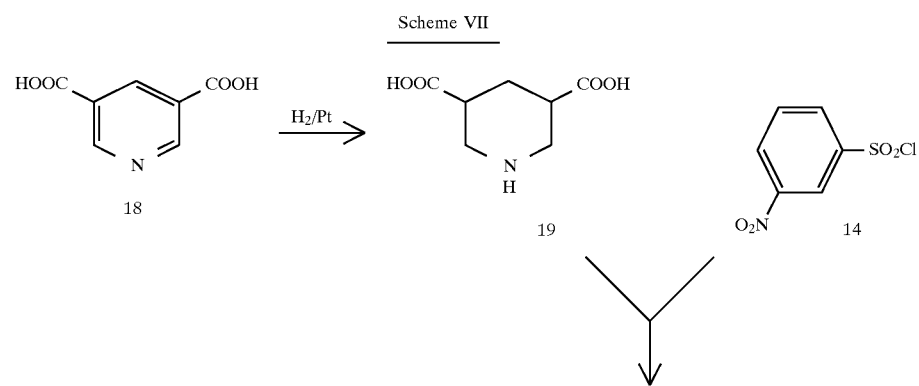

-continued
Scheme VII

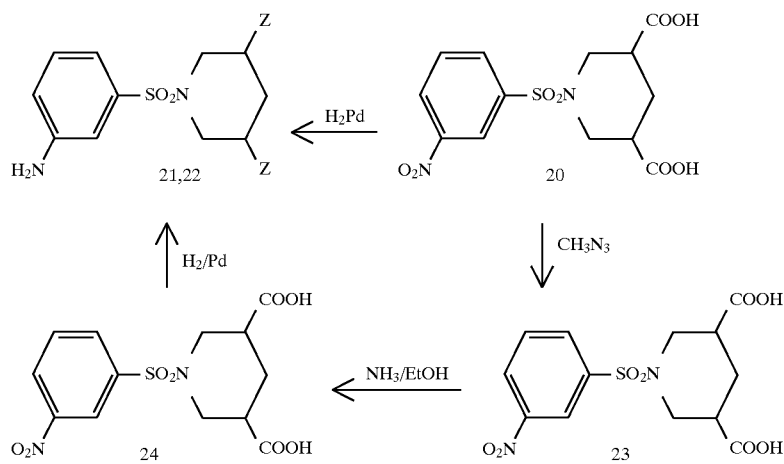

This invention also includes the methods of treating a mammal, preferably a human, experiencing a viral infection, the methods comprising administering to the mammal so afflicted one or more of the compounds of this invention, and/or one or more pharmaceutically acceptable salts of the compounds. Viral infections treatable using the compounds and methods of this invention include those infections brought on by human respiratory syncytial virus, herpes simplex viruses, human cytomegalovirus, and influenza viruses, particularly parainfluenza virus 3.

The compounds of this invention may be administered to the mammal in need thereof in any manner prescribed, including intranasally, orally, topically, transdermally, parenterally and intraperitoneally. It is understood that treating the mammal, preferably the human, will require varying dosages of active compound and varying regimens of treatment depending upon various factors including the age, sex, size, general health and extent of disorder seen in the given individual, the dosage and regimen to be determined by the proper medical practitioner. An antivirally effective amount of the compounds herein to be administered will generally range from about 0.5 mg/kg to about 500 mg/kg of animal body weight in one or more doses per day. The doses are preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. The compounds of this invention may be given with or without other antiviral agents.

The present invention also includes pharmaceutical compositions which may be used with these methods of treatment. The pharmaceutical compositions may comprise one or more of the compounds of this invention, or pharmaceutically acceptable salts thereof, and one or more pharmaceutically acceptable carriers, diluents, excipients, fillers, binders, flavoring agents, etc. For oral administration, the compositions containing the compounds of this invention include solid or liquid compositions, such as capsules, troches, lozenges, pills, tablets, powders, melts, solutions, suspensions and emulsions. The solid forms may be encapsulated by hard or soft gelatin capsules and may contain commonly used pharmaceutical acceptable excipients, fillers, adjuvants, diluents, lubricants, disintegrants, suspending or stabilizing agents, and binding agents including, but not limited to, magnesium stearate, sodium lauryl sulfate, microcrystalline cellulose, polyvinylpyrrolidone, gelatin, alginic acid, acacia gum, sodium citrate, complex silicates, calcium carbonate, glycine, dextrin, sucrose, sorbitol, calcium phosphate, dicalcium phosphate, calcium sulfate, lactose, kaolin, mannitol, sodium chloride, talc, dry starch (e.g. corn, potato or tapioca starch) and powdered sugar. The formulations may also include antioxidants, for example, vitamin E, ascorbic acid, BHT and BHA. Such pharmaceutical preparations may contain, for example, from about 0.05 up to about 90% of the active ingredient in combination with the carrier, more usually between about 5% and 60% by weight.

Suitable excipients for liquid oral formulations include diluents such as water, and alcohols such as ethanol, benzyl alcohol, and polyethylene alcohols, with or without a surfactant, suspending agent or emulsifying agent. Dispersions can be prepared in glycerol, liquid polyethylene glycols and mixtures thereof in oils. Under ordinary conditions of storage and use, these preparations contain a preservative to prevent the growth of microorganisms.

The compounds of this invention may also be administered parenterally as an injectable dosage form in a physiologically acceptable diluent such as sterile liquids or mixtures thereof water, including water, saline, aqueous dextrose and other pharmaceutically acceptable sugar solutions, alcohols such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, a pharmaceutically acceptable oil, fatty acid, fatty acid ester or glyceride, or an acetylated fatty acid glyceride with or without the addition of a pharmaceutically acceptable surfactant, such as a soap or detergent, suspending agent such as pectin, carbomers, methylcellulose, hydroxypropylmethylcellulose, or carboxymethylcellulose, an emulsifying agent or pharmaceutical adjuvants. In all cases, the form must be sterile and must be fluid to the extent that easy syringability exists. It must be stable under the conditions of manufacture and storage and must be preserved against the contaminating action of micro-organisms such as bacteria and fungi.

Pharmaceutically acceptable oils which are useful in the formulation herein include those of petroleum, animal, vegetable or synthetic origin, including peanut oil, soybean oil, sesame oil, cottonseed oil, olive oil, sunflower oil, petrolatum, and mineral oil. Fatty acids which may be used include oleic acid, stearic acid, and isostearic acid, while the fatty acid esters useful herein may include ethyl oleate and isopropyl myristate. Suitable soaps include fatty acid alkali metal, ammonium, and triethanolamine salts. Acceptable detergents include cationic detergents, for example, dimethyl dialkyl ammonium halides, alkyl pyridinium halides, and alkylamine acetates and anionic detergents, such as alkyl, aryl, and olefin sulfonates, alkyl, olefin, ether and monoglyceride sulfates, and sulfosuccinates. Useful nonionic detergents may include fatty amine oxides, fatty acid alkanolamides and polyoxyethylenepolypropylene copolymers. Amphoteric detergents may include alkyl-beta-aminopropionates and 2-alkylimidazoline quaternary salts, and mixtures thereof.

The parenteral compositions of this invention preferably will contain from about 0.5 to about 25% by weight of the active compounds described herein in solution. The parenteral formulations in the form of sterile injectable solutions or suspensions will also preferably contain from about 0.05% to about 5% suspending agent in an isotonic medium. Buffers and preservatives may be added. A suitable surfactant may also be added. These surfactants may include polyethylene sorbitan fatty acid esters, such as sorbitan monooleate, and the high molecular weight adducts of ethylene oxide with a hydrophobic base, formed by the condensation of propylene oxide with propylene glycol.

The pharmaceutical compositions of this invention also include those useful for topical and transdermal administration. These formulations may include the dermal application of the compounds of this invention in a solvent system noted for enhancing transdermal absorption, including ethanol or dimethylsulfoxide, with or without other excipients. Preferably the topical and transdermal compositions herein comprise the addition of the compounds of this invention into a patch of the reservoir and porous membrane type or in a patch of the solid matrix variety. Transdermal patches of these types are described in U.S. Pat. Nos. 3,742,951, 3,797,494, 3,996,934, 4,031,894, 4,573,996, and 4,956,171.

The intranasal formulations and administrations of this invention may be administered as intranasal drops or as an intranasal spray, such as an inhalant. The formulations may include any combination of pharmaceutically acceptable components which are useful in intranasal administration, including sterile water, saline, a stabilizing agent, such as polyethylene glycol having a molecular weight in the range of from about 200 to about 7500, or mixtures thereof.

The compounds of this invention can be used to treat viral infections either prophylactically or therapeutically. For prophylactic use, a compound could be administered intranasally as a spray or a mist or as drops on a daily basis to prevent infection by virus, in particular by RSV. The length of time during which treatment would be carried out will reflect the likelihood of infection by a specific viral agent and may be affected by epidemic situations and the risk factors displayed by a given patient. Compounds delivered in these ways may range in concentration from 0.1 to 30 mg/ml, the volume delivered ranging from 0.1 to 1 ml/nostril. Alternatively, the compounds can be delivered systemically by oral or intravenous dosing. For therapeutic use, the compounds may be delivered topically to the lungs as an aerosol or could be delivered systemically by oral or intravenous dosing. Such dosing may be administered for a period of time necessary to control the viral infection.

The compounds of this invention and their preparation can be understood further by the following non-limiting examples. The reaction intermediates, products and potential by-products are analyzed by thin-layer chromatography (TLC) on silica gel using of propan-2-ol-ethyl acetate-4% ammonia in water (8:1:1, v/v) as solvent, and reversed-phase high-performance liquid chromatography (RP-HPLC) [column: Vydac $C_{18}$ (4.6 mm×25 cm), 5 mm; mobil phase: A-acetonitrile, B-0.1M ammonium acetate in water (pH 5.5), C-methanol; gradient: from mixture A-B-C (20:65:15, v/v) to mixture A-B-C (20:55:25, v/v) in 10 minutes]. Preparative RP-HPLC is performed on a Rainin gradient HPLC system using a Vydac C18 Peptide/Protein preparative column (10 mm, 22 mm×25 cm); mobil phase: A-methanol-0.1M ammonium acetate in water (pH 5.5) (1:4, v/v) B-methanol-acetonitrile (1:4, v/v); gradient: 18–32% B in 10 minutes.

EXAMPLE 1

4,4'-Bis[4.6-di[3-aminophenyl-N,N-bis(2-carbamoyl-ethyl)sulfonylimino]-1,3,5-triazin-2-ylamino]-stilbene-2,2'-disulfonic acid, disodium salt A solution of cyanuric chloride (3.87 g, 21 mmole) in dioxane (25 ml) was added to phosphate buffer (100 ml, 0.3M, pH 7) with stirring at −3°–0° C. A solution of 4,4'-diaminostilbene-2,2'-disulfonic acid (3.70 g, 10 mmole) in 1N NaOH (20 ml) was then added over a 20 minute period and the pH maintained at 6.5–7.2 by addition of 1N NaOH. Stirring was continued for a further 1 hour at the same temperature and pH while the reaction was monitored for completeness by analytical HPLC (yield 95%). A solution of 3-aminophenyl-N,N-bis(2-carbamoylethyl)sulfonylimine (13.20 g, 42 mmole)(G.B. U.S. Pat. No. 1,194,388; Jun. 10, 1970) in dimethylsulfoxide(DMSO) (100 ml) was added over a 20 minute period and the temperature raised to 50° C. Stirring was continued for 2.5 hours at this temperature and then for 40 hours at 100°–110° C. with the pH maintained at 6.6–7.2 by addition of 1N NaOH. Once the reaction was complete as determined by analytical HPLC (or TLC), the mixture was cooled to 20° C. and acidified with 5.6N hydrochloric acid to pH 2. Sodium chloride (60 ml, 4M) was added and the precipitated product filtered, redissolved in a minimum volume of water by addition of 1N NaOH to pH 7 and re-precipitated by the addition of sodium chloride. The precipitate was filtered, washed with cold water (20 ml), propan-2-ol (40 ml), acetone (60 ml) and dried under vacuum at 50° C. Yield 13.0 g (72%)., m.p. >250° C. dec; UV(water): 273 nm (log$\epsilon$5.11), 350 nm (log$\epsilon$ 4.89); MS(ES) (m/z): $M^{-2}$ 887.9; MW 1821.2.

EXAMPLE 2

4,4'-Bis[4,6-di[3-aminophenyl-N,N-bis(2-carbamoyl-ethyl)sulfonylimino]-1,3,5-triazin-2-ylamino]-stilbene-2,2'-disulfonic acids, disodium salt A suspension of 4,4'-diaminostilbene-2,2'-disulfonic acid, disodium salt (1.21 g, 2.92 mmole) and 2-chloro-4,6-di[3-aminophenyl-N,N-bis(2-carbamoylethyl)-sulfonylimino]-1,3,5-triazin (Example 6) (4.47 g, 6.44 mmole) in sulfolane (70 ml) and diisopropylethylamine (1.5 ml) was warmed in a sealed thick-walled glass tube to 115° C. Warming was continued for 40 hours. Once the reaction was complete as determined by analytical HPLC (or TLC), the mixture was cooled to 30° C., 1N NaOH (6.6 ml) was added and the product precipitated by the addition of propan-2-ol (200 ml).

The precipitate was filtered, washed with acetone (30 ml) and redissolved in a minimum volume of water and re-precipitated by the addition of ethanol. The precipitate after filtration was washed with ether (30 ml) and dried under vacuum at 50° C. Yield 4.84 g (91%).

EXAMPLE 3

4,4'-Bis[4.6-di[3-aminophenyl-N,N-bis(2-carbamoyl-ethyl)sulfonylimino]-1.3.5-triazin-2-ylamino]-stilbene-2,2'-disulfonic acid, disodium salt The title compound was prepared using the general conditions of Example 1, where 2,4,6-trifluoro-1,3,5-triazine (304 mg, 2.25 mmole) was reacted with 4,4'-diaminostilbene-2,2'-disulfonic acid (455 mg, 110 mmole) for 1 hour, and then with 3-aminophenyl-N,N-bis(2-carbamoylethyl)sulfonylimine (1.45g, 4.62 mmole)(G.B. U.S. Pat. No. 1,194,388; Jun. 10, 1970), followed by purification, to give the desired compound (1,21 g, 61%).

The compounds synthesized by procedures of Examples 1–3 are identical according to HPLC, UV and mass-spectra.

EXAMPLE 4

4,4'-Bis[4,6-di[3-aminophenyl-N,N-bis(2-carbamoyl-ethyl)sulfonylimino]-1,3,5-triazin-2-ylamino]-biphenyl-2,2'-disulfonic acid, disodium salt The title compound was prepared according to the procedure of Example 2 using 4,4'-diaminobiphenyl-2,2'-disulfonic acid, disodium salt (1.02 g, 2.62 mmole) and 2-chloro-4,6-di[3-aminophenyl-N,N-bis(2-carbamoylethyl)sulfonilimino]-1,3,5-triazine (Example 6) (4.26 g, 5.76 mmole). in 60 ml DMSO-sulfolane (1:3, v/v) and diisopropylethylamine (1.2 ml). The product was obtained as a colorless solid (3.90 g, 83%); m.p. >250° C. dec; UV(water): 272 nm (logε 4.86); MS(ES) (m/z): $M^{-2}$ 874.1; MW 1794.2.

EXAMPLE 5

4,4'-Bis[4,6-di[3-aminophenyl-N,N-bis(2-hydroxyethyl)sulfonylimino]-1,3,5-triazin-2-ylamino]-stilbene-2,2'-disulfonic acid, disodium salt The tide compound was prepared according to the procedure used to prepare Example 2 using 4,4'-diaminostilbene-2,2'-disulfonic acid (28 mg, 0.075 mmole) and 95 mg (0.15 mmole) of 2-chloro-4,6-di[3-aminophenyl-N,N-bis(3-hydroxyethyl)sulfonilimino]- 1,3,5-triazine (Example 6) in sulfolane (20 ml) and diisopropylethylamine (35 ml) at 110° C. for 18 hours. The cooled reaction mixture was mixed with deionised water (40 ml) and the solution of crude product was purified by preparative RP-HPLC. Fractions containing the desired product are combined, organic solvents are evaporated under vacuum (10 mm Hg) at 30° C., and the product was concentrated, desalted and isolated via octadecyl (C18) cartridge (900 mg, obtained from Burdick & Jackson). The cartridge was washed with water (30 ml) and the product reextracted with methanol (50 ml). Evaporation of the methanol gave 12 mg (11%) of the desired product; m.p. >250° C. dec; UV(water): UV(water): 273 nm (logε 4.97),350 nm (logε 4.81); MS(ES) (m/z): $M^{-2}$ 779.0; MW 1604.0.

EXAMPLE 6

2-Chloro-4,6-di[3-aminophenyl-N,N-bis(2-carbamoyl-ethyl)sulfonylimino]-1,3,5-triazine A solution of cyanuric chloride (4.2 g, 22.7 mmole) in dioxane (55 ml) was added dropwise with stirring to phosphate buffer (120 ml, 0.3M, pH 7) and crushed ice (10 g) at −2°–0° C. To the resulting fine suspension was added dropwise over a 30 minute period a solution of 3-aminophenyl-N,N-bis(2-carbamoylethyl)sulfonylimine (15.0 g, 47.8 mmole) (G.B. U.S. Pat. No. 1,194,388; Jun. 10, 1970) in N,N-dimethylformamide (125 ml) and the pH maintained at 6.5–7.2 by addition of 1N NaOH. Stirring was continued for a further 1 hour (0° C., pH 7.0) and the temperature raised to 55° C. Stirring was continued for 2.5 hours while the reaction is monitored for completeness by analytical HPLC (or TLC). Once the reaction was complete as determined by analytical HPLC (or TLC), the mixture was cooled to 0° C., water (160 ml) was added and the product precipitate filtered, washed with cold water (50 ml), acetone (50 ml) and dried under vacuum at 40° C. Yield 14.5 g (86%); m.p. >250° C. dec; UV(DMSO): 282 nm (logε 4.77); MS(CI) (m/z): MH 740.1.

EXAMPLE 7

4-[4.6-Di[3-aminophenyl-N,N-bis(2-carbamoylethyl)sulfonylimino]-1,3,5-triazin-2-ylamino]-4'-[4-chloro-6-8 3-aminophenyl-N,N-bis(2-carbamoylethyl)sulfonylimino-]-1,3,5-triazin-2-ylamino]-stilbene-2,2'-disulphonic acid, disodium salt A solution of cyanuric chloride (205 mg, 1.12 mmole) in dioxane (1.5 ml) was added to phosphate buffer (10 ml, 0.3M, pH 7) with stirring at −3°–0° C. A solution of 4,4'-diaminostilbene-2,2'-disulfonic acid, disodium salt (225 mg, 0.54 mmole) in phosphate buffer (3 ml) was added and the pH maintained at 6.5–7.2 by addition of 1N NaOH. Stirring was continued for a further 1 hour at the same temperature and pH while the reaction was monitored for completeness by analytical HPLC (yield 97%). A solution of 3-aminophenyl-N,N-bis(2-carbamoylethyl)sulfonylimine (700 mg, 2.23 mmole) in N,N-dimethylformamide (10 ml) was added over a 10 minute period and the temperature raised to 60° C. Stirring was continued for 3 hours at this temperature and 20 hours at 100°110° C. with the pH maintained at 6.6–7.2 by addition of 1N NaOH. Once the reaction was complete as determined by analytical HPLC, the mixture was cooled to 20° C. and acidified with 5.6N hydrochloric acid to pH 2, sodium chloride (5 ml, 4M) was added and the product precipitate filtered, washed with cold water (2 ml), and dried under vacuum at 40° C. Two portions of a solution of crude product (about 1 g) in deionised water (250 ml) were purified separately by preparative RP-HPLC. Fractions containing the desired product were combined, organic solvents were evaporated under vacuum (10 mm Hg) at 30° C., and the product was concentrated, desalted and isolated via octadecyl (C18) cartridge (900 mg, obtained from Burdick & Jackson). The cartridge was washed with water (30 ml) and the product reextracted with methanol (50 ml). Evaporation of the methanol gives 268 mg (32%) of the desired product, m.p. >250° C. dec; UV(water): 273 nm (logε 4.83), 350 nm (logε 4.44); MS(ES) (m/z): $M^{-2}$ 749.15; MW 1544.3.

EXAMPLE 8

4,4'-Bis[4-chloro-6-[3-aminophenyl-N,N-bis(2-carbamoylethyl)sulfonylimino]-1,3,5-triazin-2-ylamino]-stilbene-2,2'-disulphonic acid, disodium salt A solution of cyanuric chloride (0.91 g, 4.95 mmole) in dioxane (8 ml) was added to phosphate buffer (30 ml, 0.3M, pH 7) with stirring at −3°–0° C. A solution of 4,4'-diaminostilbene-2,2'-disulfonic acid, disodium salt (1.00 g, 2.41 mmole) in deionised water (9 ml) is added and the pH maintained at 6.5–7.2 by addition of 1N NaOH. Stirring was continued for a further 1 hour at the same temperature and pH while the reaction was monitored for completeness by analytical HPLC (yield 98%). A solution of 3-aminophenyl-N,N-bis(2-carbamoylethyl)sulfonylimine (1.57 g, 5.00 mmole) in N,N-dimethylformamide (25 ml) was added over a 10-min period and the temperature raised to 50° C. Stirring was continued for 6 hours at this temperature with the pH maintained at 6.6–7.2 by addition of 1N NaOH. Once the reaction was determined complete by analytical HPLC (or TLC), the mixture was cooled to 0° C. and acidified with 5.6N hydrochloric acid to pH 2. Sodium chloride (5 ml, 4M) was added and the product precipitate filtered, washed with cold water (8 ml), acetone (20 ml) and ether (20 ml), and dried under vacuum at 40° C. Yield 2.37 g (80%)., m.p. >300° C. dec; UV(water): 273 nm (log$\epsilon$ 4.57), 350 (log$\epsilon$ 4.42); MS(ES) (m/z): $M^{-2}$ 610.1; MW 1266.2.

EXAMPLE 9

4-[4,6-Di[3-aminophenyl-N,N-bis(2-carbamoylethyl)sulfonylimino]-1,3,5-triazin-2-ylamino]-4'-[4-[3-aminophenyl-N,N-bis(2-carbamoylethyl)sulfonylimino]-6-[3-aminophenyl-N-(2-carbamoylethyl)-N'-(3-propionic acid)]-1,3,5-triazin-2-ylamino]-stilbene-2,2'-disulphonic acid, disodium salt and

EXAMPLE 10

4-[4.6-Di[3-aminophenyl-N,N-bis(2-carbamoylethyl)sulfonylimino]-1,3,5-triazin-2-ylamino]-4'-(4-[3-aminophenyl-N,N-bis(2-carbamoylethyl)sulfonylimino]-6-[3-aminophenyl-N,N bis(3-propionic acid)-1,3,5-triazin-2-ylamino]-stilbene-2,2'-disulphonic acid, disodium salt To a solution of Example 1 (200 mg, 0.11 mmole) in deionised water (20 ml) was added 1N NaOH (300 ml) and the mixture heated to boiling. The reaction mixture was kept warm for 3 hours, cooled to 0° C. and acidified with 5.6N hydrochloric acid to pH 2. Sodium chloride (10 ml, 4M) was added and the product precipitate filtered, washed with cold water (2 ml), and dried under vacuum at 40° C. A solution of crude product (about 180 mg) in distilled water (125 ml) was purified by preparative RP-HPLC. Fractions containing the desired product (Example 9) are combined, organic solvents are evaporated under vacuum (10 mm Hg) at 30° C., and the product was concentrated, desalted and isolated via octadecyl (C18) cartridge (900 mg, obtained from Burdick & Jackson). The cartridge was washed with water (30 ml) and the product reextracted with methanol (50 ml). Evaporation of the methanol yielded 24 mg (12%) of the desired product., m.p. >250° C. dec; UV(water): 273 nm (log$\epsilon$5.02), 350 nm (log$\epsilon$ 4.76); MS(ES) (m/z): $M^{-2}$ 888.3; MW 1822.6.

The second product (Example 10) is isolated from the other fractions containing the desired compound (Example 10) by RP-HPLS-separation while using the same procedure of concentration, desalting and isolation via octadecyl ($C_{18}$) cartridge described in Example 9. Yield 18 mg (9%), m.p. >250° C. dec, UV(water) 273 nm (log$\epsilon$ 4.92), 350 (log$\epsilon$ 4.69); MS(ES) (m/z): $M^{-2}$ 889.2; MW 1824.4.

EXAMPLE 11

4,4'-Bis[4,6-di[3-aminophenyl-N,N-bis(2-carbamoyl-ethyl)sulfonylimino]-1,3,5-triazin-2-ylamino]-bibenzyl-2,2'-disulfonic acid, disodium salt A solution of Example 1 (30 mg) in 30 ml water-methanol (1:1, v/v) was stirred with palladium on charcoal (10% Pd) in a hydrogen atmosphere for 5 days. The reaction mixture was filtered and the solvent evaporated. The product was isolated by preparative RP-HPLC. The fractions containing the desired product were combined, organic solvents evaporated under vacuum (10 mm Hg) at 30° C., and the product isolated via octadecyl (C18) cartridge (300 mg, obtained from Burdick & Jackson). The cartridge was washed with water (30 ml) and the product reextracted with methanol (50 ml). Evaporation of the methanol left 16 mg (50%) of the desired product; m.p.>250° C. dec; UV(water): 274 nm (log$\epsilon$ 4.96); MS(ES) (m/z): $M^{-2}$ 889.2; MW 1824.4.

EXAMPLE 12

4,4'-Bis[4,6-di[4-aminophenyl-N,N-bis(2-carbamoylethyl)sulfonylimino]-1,3,5-triazin-2-ylamino]-stilbene-2,2'-disulfonic acids, disodium salt The title compound was prepared according to the procedure used for the synthesis of Example 2 using 4,4'-diaminostilbene-2,2'-disulfonic acid (48 mg, 0.125 mmole) and 2-chloro-4,6-di[4-aminophenyl-N,N-bis(2-carbamoylethyl)sulfonylimino]-1,3,5-triazine (Example 18) (230 mg, 0.310 mmole) in dimethylsulfoxide (12 ml) and diisopropylethylamine (260 ml). The product was obtained as a colorless solid (173 mg, 77%); m.p.>250° C. dec; UV(water): 296 nm (log$\epsilon$ 4.94), 352 nm (log$\epsilon$ 4.57); MS(ES) (m/z): $M^{-2}$ 883.2; MW 1822.4.

EXAMPLE 13

4.4'-Bis[4.6.di[4-aminophenyl-N,N-bis(2-carbamoylethyl)sulfonylimino]-1,3,5-triazin-2-ylamino]-biphenyl-2,2'-disulfonic acid, disodium salt The title compound was prepared according to the procedure used for the synthesis of Example 2 using 4,4'-diaminobiphenyl-2,2'-disulfonic acid, disodium salt (113 mg, 0.33 mmole) and 2-chloro-4,6-di[4-aminophenyl-N,N-bis(2-carbamoylethyl)sulfonylimino]-1,3,5-triazine (Example 18) (535 mg, 0.72 mmole) in 25 ml DMSO-sulfolane (2:3, v/v) and diisopropylethylamine (350 ml). The product was obtained as a colorless solid (450 mg, 76%); m.p.>250° C. dec; UV(water): 296 nm (log$\epsilon$ 5.13); MS(ES) (m/z): $M^{-2}$ 874.4; MW 1794.8.

EXAMPLE 14

2-Chloro-4,6-di(3'-sulfoamidoanilino)-1,3,5-triazine

A solution of cyanuric chloride (2.37 g, 12.9 mmole) in acetone (25 ml) was added dropwise with stirring to phosphate buffer (60 ml, 0.3M, pH 7) at −2°–0° C. To the resulting fine suspension was added dropwise over a 20 minute period, a solution of m-sulfanilamide (4.35 g, 25.3 mmole) in acetone (30 ml) and the pH maintained at 6.5–7.2 by addition of 1N NaOH, Stirring was continued for a further 30 min (0° C., pH 7.0) and the temperature raised to 55° C. Stirring was continued for 3 hours, while the reaction was monitored for completeness by analytical HPLC (or TLC). Once the reaction was complete as determined by analytical HPLC (or TLC), the mixture was cooled to 0° C., water (100 ml) was added and the product precipitate filtered, washed with cold water (50 ml), dried on the filter, and purified by dissolving in hot acetone (40 ml) and precipitation with benzene (150 ml). The product was filtered, washed with propan-2-ol (20 ml) and ether (30 ml), dried under vacuum at 30° C. Yield 3,72 g (64%); m.p.>250° C. dec; UV(MeOH): 277 nm (logε 4.68); MS(CI) (m/z): MH 456.0.

EXAMPLE 15

4,4'-Bis[4.6-di[3-aminophenylsulphonylamido]-1,3, 5-triazin-2-ylamino]-stilbene-2,2'-disulfonic acid, disodium salt The title compound was prepared according to the procedure used to prepare Example 2 using 4,4'-diaminostilbene-2,2'-disulfonic acid, disodium salt (216 mg, 0.52 mmole) and 2-chloro-4,6-di(3'-sulfoamidoanilino)-1,3, 5-triazine (Example 14) (524 mg, 1.15 mmole) in sulfolane (15 ml) and diisopropylethylamine (250 ml,) for 40 hours at 115° C. After cooling to 20° C., the reaction mixture was diluted with ether (100 ml) and 1N NaOH (2.08 ml) added. After centrifugation, the residue was stirred with propan-2-ol (50 ml) until crystallization was complete. The solid was centrifuged, washed with methanol (2×30 ml) and ether (2×30 ml), and dried under vacuum at 30° C. Yield (570 mg, 92%); m.p.>250° C. dec; UV(water): 273 nm (logε 4.76), 350 nm (logε 4.52).

EXAMPLE 16

4,4'-Bis[4,6-di[3-aminophenylsylphonylimido]-1,3, 5-triazin-2-ylamino]-biphenyl-2,2'-disulfonic acid, disodium salt The title compound was prepared according to the procedure used to prepare Example 2 using 4,4'-diaminobiphenyl-2,2'-disulfonic acid (208 mg, 0.60 mmole) .and 2-chloro-4,6-di(3'-sulfoamidoanilino)-1,3,5-triazine (Example 14) (607 mg, 1.33 mmole) in sulfolane (20 ml) and diisopropylethylamine (850 ml,) for 40 hours at 115° C. After cooling to 20° C., the reaction mixture was diluted with ether (150 ml) and 1N NaOH (2.40 ml) added. After centrifugation, the residue was stirred with propan-2-ol (50 ml) until crystallization was complete. The solid was centrifuged, washed with methanol (40 ml) and ether (2×20 ml), and dried under vacuum at 30° C. Yield (505 mg, 72%); m.p.>250° C. dec; UV(water): 276 nm (logε 4.93).

EXAMPLE 17

4,4'-Dihydroxybiphenyl-2,2'-disulfonic acid

To a suspension of 4,4'-diaminobiphenyl-2,2'-disulfonic acid (4.44 g, 12.9 mmole) in water (20 ml) was added a solution of sodium carbonate (8.6 ml, 1.5M) by warming until a clear solution was obtained. After cooling to 5° C., to this solution was added a solution of sodium nitrite (1.78 g, 12.9 mmole) in water (3 ml). The resulting solution was added dropwise with stirring to a solution of concentrated sulfuric acid (3.8 ml) in water (13 ml) and crushed ice (10 g) at −5°—−2° C. Stirring was continued for a further 30 minutes, and the reaction mixture was warmed to 65° C. The temperature was maintained until nitrogen evolution takes place. The mixture was cooled to 10° C. and neutralized with dry sodium carbonate, and the solution evaporated to a residue. The residue was dried under vacuum at 50° C., mixed with ethanol (225 ml) and filtered. The filtrate was evaporated and dried under vacuum at 40° C. Yield 3.88 (87%). m.p.>250° C. dec; UV(0.05N NaOH): 252 nm (logε 4.16), 311 mn (logε 3.40); MS(ES) (m/z): $(M-H)^{-1}$ 345.0; MW 346.0.

EXAMPLE 18

2-Chloro-4,6-di[4-aminophenyl-N,N-bis(2-carbamoylethyl)sulfonylimino]-1,3,5-triazine The title compound was prepared according to the procedure used to prepare Example 6 using 4-aminophenyl-N, N-bis(carbamoylethyl)sulfonylimine (3.3 g, 10,5 mmole) (G.B. U.S. Pat. No. 1,194,388; Jun. 10, 1970) and cyanuric chloride (1.0 g, 5.4 mmole). The product was obtained as a colorless solid (3.5 g, 88%); m.p.>250° C. dec; UV(DMSO): 303 nm (logε 4.84); MS(CI) (m/z): MH 740.1.

EXAMPLE 19

4,4'-Bis[4,6-di[3-aminophenyl-N,N-bis(2-carbamoylethyl)sulfonylimino]-1,3,5-triazin-2-yloxy]-biphenyl-2,2'-disulfonic acid, disodium salt A suspension of 4,4'-dihydroxybiphenyl-2,2'-disulfonic acid (Example 17) (131 mg, 0.34 mmole) and 2-chloro-4, 6-di[3-aminophenyl-N,N-bis(2-carbamoylethyl) sulfonylimino]-1,3,5-triazine (Example 6) (550 mg, 0.74 mmole) in sulfolane-N,N-dimethylformamide (15 ml, 2:1 v/v) and NaOH (1N, 1.48 ml) was warmed in a sealed thick-walled glass tube to 115° C. Warming was continued for 50 hours. Once the reaction was complete as determined by analytical HPLC (or TLC), the mixture was cooled to 20° C., and the product precipitated by addition of propan-2-ol (70 ml), washed on filter with cold ethanol (15 ml), and dried under vacuum at 40° C. Two portions of a solution of crude product (about 0.6 g) in deionised water (200 ml) were purified separately by preparative RP-HPLC. Fractions containing the desired product were combined, organic solvents evaporated under vacuum (10 mm Hg) at 30° C., and the product concentrated, desalted and isolated via octadecyl (C18) cartridge (900 mg, obtained from Burdick & Jackson). The cartridge was washed with water (30 ml) and the product reextracted with methanol (50 ml). Evaporation of the methanol gives 171 mg (28%) of the desired product; m.p.>250° C. dec; UV(water): 272 nm (logε 4.86); MS(ES) (m/z): $M^{-2}$ 875.2; MW 1796.4.

EXAMPLE 20

5,5'-Dimethyl-4,4'-bis[4,6-di[3-aminophenyl-N,N-bis(2-carbamoylethyl)sulfonylimino]-1,3,5-triazin-2-ylamino]-biphenyl-2.2'-disulfonic acid, disodium salt The compound was prepared according to the procedure used to prepare (Example 2) using 5,5'-dimethyl-4,4'-diaminobiphenyl-2,2'-disulfonic acid, disodium salt (206 mg, 0.49 mmole) and 2-chloro-4,6-di[3-aminophenyl-N,N-bis(2-carbamoylethyl) sulfonylimino]-1,3,5-triazine (Example 6) (805 mg, 1.08 mmole) in 30 ml DMSO-sulfolane (1:1, v/v) and diisopropylethylamine (200 ml) for 50 hours at 115° C. The product after HPLC-purification was obtained as a colorless solid (191 mg, 22%); m.p.>250° C. dec; UV(water): 274 nm logε 5.08); MS(ES) (m/z): $M^{-2}$ 8883.3; MW 1822.6.

EXAMPLE 21

2-Chloro-4,6-di[3-aminophenyl-N,N-bis(3-hydroxyethyl)sulfonilimino]-1,3,5-triazine A solution of cyanuric chloride (135 mg, 0.73 mmole) in dioxane (55 ml) was added dropwise with stirring to phosphate buffer (120 ml, 0.3M, pH 7) and crushed ice (10 g) at from −20° to 0° C. To the resulting fine suspension was added dropwise over a 20 minute period a solution of 3-aminophenyl-N,N-bis(2-hydroxyethyl) sulfonylimine (365 mg, 1.40 mmole) in N,N-dimethylformamide (125 ml) and the pH maintained at 6.5–7.2 by addition of 1N NaOH. Stirring was continued for a further 1 hour (0° C., pH 7.0)

and the temperature raised to 55° C. Stirring was continued for 2.5 hours, while the reaction was monitored for completeness by analytical HPLC (or TLC). Once the reaction was complete as determined by analytical HPLC (or TLC), the mixture was cooled to 0° C., water (160 ml) was added and the product precipitate filtered, washed with cold water (50 ml), acetone (50 ml) and dried under vacuum at 40° C. Yield 395 mg (89%); m.p.>250° C. dec; UV (DMSO): 284 nm.

EXAMPLE 22

4,4'-Bis[4.6-di[3-aminophenyl-N,N-bis(2-hydroxyethyl)sulfonyliminol-1,3,5-triazin-2-ylamino]-biphenyl-2,2'-disulfonic acid, disodium salt This compound was prepared according to the procedure used to prepare Example 2 using 4,4'-diaminobiphenyl-2,2'-disulfonic acid (28 mg, 0.08 mmole) and 115 mg (0.17 mmole) of 2-chloro-4,6-di[3-aminophenyl-N,N-bis(3-hydroxyethyl)sulfonylimino]-1,3,5-triazine (Example 21) in sulfolane (10 ml) and diisopropylethylamine (25 ml) at 110° C. for 18 hours. The product after HPLC-purification was obtained as a colorless solid (16 mg, 13%); m.p.>250° C. dec; UV(water): 272 nm (logε 4.88); MS(ES) (m/z): $M^{-2}$ 776.0; MW 1534.0.

EXAMPLE 23

9.9-Dioxo-2,7-Bis[4,6-di[3-aminophenyl-N,N-bis(2-carbamoylethyl)sulfonylimino]-1,3,5-triazin-2-ylamino]-dibenzothiophen-3.6-disulfonic acid, disodium salt The title compound was prepared according to the procedure used to prepare Example 1 using a solution of cyanuric chloride (59 mg, 0.32 mmole), 9,9-dioxo-2,7-diamino-dibenzothiophen-3,6-disulfonic acid (77 mg, 0.16 mmole) and 2-chloro-4,6-di[4-aminophenyl-N,N-bis(2-carbamoylethyl)sulfonylimino]-1,3,5-triazine (Example 6) (300 mg, 0.96 mmole) in dioxane (15 ml) and phosphate buffer (20 ml, 0.3M, pH 7) at 110° C. for 18 hours. The product after HPLC-purification was obtained as a colorless solid (64 mg, 11%); m.p.>250° C. dec; MS(ES) (m/z): $M^{-2}$ 905.1; MW 1858.2.

EXAMPLE 24

4,4'-Bis[4-chloro-6-di[4-amino-N'-[3-aminophenyl-N,N-bis(2-carbamoylethyl)sulfonylimino]-benzamide]-1,3,5-triazin-2-ylamino]-stilbene-2,2'-disulfonic acid, disodium salt The compound was prepared according to the procedure used to prepare Example 2 using 4,4'-diaminostilbene-2,2'-disulfonic acid (20 mg, 0.054 mmole) and 112 mg (0.12 mmole) of 2,4-dichloro-6-[4-amino-N'-[3-aminophenyl-N,N-bis(2-carbamoylethyl)sulfonylimino]-benzamide]-1,3,5-triazin (Example 26) in sulfolane (20 ml) and diisopropylethylamine (38 ml) at 110° C. for 18 hours. The product after HPLC-purification was obtained as a colorless solid (20 mg, 23%); m.p.>25° C. dec; UV(water): 295 nm (logε 4.54), 350 nm (logε 4.39); MS(ES) (m/z): $M^{-2}$ 727.1; MW 1482.2.

EXAMPLE 25

4,4'-Bis[4,6-di[4-amino-N'-[3-aminophenyl-N,N-bis(2-hydroxyethyl)sulfonylimino]-benzensulfoamide]-1,3,5-triazin-2-ylamino]-stilbene-2,2'-disulfonic acid, disodium salt The title compound was prepared according to the procedure used to prepare Example 2 using 4,4'-diaminostilbene-2,2'-disulfonic acid (20 mg, 0.054 mmole) and 203 mg (0.22 mmole) of 2-chloro-4,6-di[4-amino-N'-[3-aminophenyl-N,N-bis(2-hydroxylethyl)sulfonylimino]-benzensulfonamide]-1,3,5-triazin (Example 27) in sulfolane (20 ml) and diisopropylethylamine (38 ml) at 110° C. for 18 hours. The product after HPLC-purification was obtained as a colorless solid (30 mg, 25%); m.p.>250° C. dec; UV(water): 295 nm (logε 5.21), 350 nm (logε 4.69); MS(ES) (m/z): $M^{-2}$ 1089.3; MW 2226.6.

EXAMPLE 26

2,4-Dichloro-6-[4-amino-N'-[3-aminophenyl-N,N-bis(2-carbamoylethyl)sulfonylimino]-benzamide]-1,3,5-triazin A solution of cyanuric chloride (56 mg, 0.3 mmole) in dioxane (1 ml) was added with stirring to phosphate buffer (12 ml, 0.3M, pH 7) at −20° C. To the resulting suspension was added dropwise a solution of 4-amino-N'-[3-aminophenyl-N,N-bis(2-carbamoylethyl)sulfonylimino] benzamide 130 mg, 0.3 mmole) in N,N-dimethylformamide (2 ml) and the pH maintained at 6.5–7.2 by addition of 1N NaOH. Stirring was continued for a further 1 hour (0° C., pH 7.0), then water (20 ml) was added and the product precipitate filtered, washed with cold water (10 ml), acetone (5 ml) and dried under vacuum at 20° C. to give 108 mg (62%) of the desired product; m.p.>250° C. dec; UV (DMSO) ; 285 nm.

EXAMPLE 27

2-Chloro-4,6-di[4-amino-N'-[3-aminophenyl-N,N-bis(2-hydroxylethyl)sulfonylimino]-benzensulfonamide]-1,3,5-triazin The title compound was prepared according to the procedure used to prepare Example 6 using 4-amino-N'-[3-hydroxyethyl)sulfonylimino]benzenesulfonamide (125 mg, 0.31 mmole) and cyanuric chloride (28 mg, 0.15 mmole). The product was obtained as a colorless solid (105 mg, 74%); m.p.>250° C. dec; UV(DMSO): 298 nm.

EXAMPLE 28

4,4'-Dinitro-2,2'-diphenic acid 2,2'-Diphenic acid (Aldrich, 50.0 g, 206 mmoles) was added portionwise to 500 mL of 3:1 90% $HNO_3/H_2SO_4$ keeping the temperature less than 10° C. The clear solution was stirred in an ice bath for one hour, then carefully quenched over approximately 750 g ice. A white solid is isolated by vacuum filtration which is a 2:1 ratio of the isomers shown. This mixture is purified by chromatographing down 1.5 kg silica gel slurried in 8:2 isopropanolammonium hydroxide and eluted with the same solvent mixture. The product comes off the column first, practically running with the solvent front. The minor isomer comes off the column later (see P.R. 232–11). Product fractions are concentrated on the rotovap. The concentrated solution is acidified to pH 1 with HCl, and filtered to afford 31.9 g of 4,4'-dinitro-2,2'-diphenic acid. 300 Mhz NMR (DMSO d6): δ7.55 (1H, d, J=8.7); 8.45 (1H, dd, J=2.5, 8.7); 8.68 (1H, d, J=2.5). 13 (1H br s). CHN: Theory: C: 48.60% H: 2.77% N: 8.10%. Theory calculated with 0.75 moles water. Found: C: 48.68% H: 2.72% N: 7.42%

EXAMPLE 29

4,4'-Diamino-2,2'-diphenic acid 4,4'-Dinitro-2,2'-diphenic acid (Example 28, 10.0 g, 30.1 mmol; P.R. 232–9) is suspended in 90 mL water and titrated to pH 7 with saturated NaHCO$_3$ (NaOH may be used). 10% Pd/C (0.5 g; Aldrich) is added and the mixture is reduced under 30 psi H$_2$ for one hour. The catalyst is removed by filtration and the filtrate is concentrated to ~20 mL. Acetone (40 mL) is added carefully to the concentrated solution, causing precipitation of the product as the disodium salt. It is collected by vacuum filtration and dried in vacuo to afford 9.2 g of 4,4'-diamino-2,2'-diphenic acid as the disodium salt. 300 MHz NMR (D$_2$O): δ4.70 (—NH$_2$, s); 6.71 (1H, dd, J=2.4, 8.25); 6.79 (1H, d, J=2.4); 7.00 (1H, d, J=8.25). CHN: Theory: C: 49.64 H: 3.72 N: 8.27 (Calculated with 1.25 moles water). Found: C: 49.55H: 3.72N: 7.90

EXAMPLE 30

4,4'-Bis-(4,6-bis{3-[bis-(2-carbamoyl-ethyl)-sulfamoyl]-phenylamino}-1,3,5-triazin-2-ylamino]-biphenyl-2,2'-dicarboxylic acid, disodium salt A suspension of 4,4'-diaminobiphenic acid, disodium salt (Example 29, 66 mg, 0.19 mmol) and 2-chloro-4,6-di[3-aminophenyl-N,N-bis(2-carbamoylethyl)-sulfonylimino]-1,3,5-triazine (Example 6) (300 mg, 0.40 mmol) in sulfolane (10 ml) and diisopropylethylamine (0.3 ml) was warmed in a sealed thick-walled glass tube to 115° C. Warming was continued for 50 hours. Once the reaction was complete as determined by analytical HPLC (or TLC), the mixture was cooled to 20° C., and the product precipitated by addition of propan-2-ol (70 ml), washed on filter with cold ethanol (15 ml), and dried under vacuum at 40° C. Two portions of a solution of crude product (about 0.3 g) in deionised water (200 ml) were purified separately by preparative RP-HPLC. Fractions containing the desired product were combined, organic solvents evaporated under vacuum (10 mm Hg) at 30° C., and the product concentrated, desalted and isolated via octadecyl (C18) cartridge (900 mg, obtained from Burdick & Jackson). The cartridge was washed with water (20 ml) and the product reextracted with methanol (40 ml). Evaporation of the methanol gives 112 mg (34%) of the desired product; m.p.>250° C. dec; MS(ES) m/z: M$^{-2}$ 840.2; MW 1724.4.

EXAMPLE 31

3-Aminophenyl-N,N-bis(2-methoxycarbonyl-ethyl) sulfonylimine

3-Aminobenzenesulfonamide (3 g, 17.4 mmol) was dissolved in nitrobenzene (55 mL) at 100° C. Temperature was then reduced to 90° C. and methyl acrylate (5 mL, 55.5 mmol) and Triton B (0.4 mL, 40% in MeOH) was added. The reaction vessel was equipped with a strong condensor and allowed to run for 20 hours. TLC showed the completeness of the reaction. A solution of HCl (30 mL, 1M in diethyl ether) was added to the reaction mixture to produce a sticky oil. This was dissolved in 50% ethyl acetate/hexane and loaded onto a silica gel column. The desired product was eluted with hexane. The solvent was evaporated to give 3.9 g (65%) of the desired product; (m/z): MH 343.2, mp 59°–60° C.

EXAMPLE 32

3-Aminophenyl-N,N-bis-(2-methylcarbamoyl-ethyl) sulfonylimine

To a solution of methyl amine (10 mL, 8.03M, 33% in ethanol) was added a solution of 3-aminophenyl-N,N-bis(2-methoxycarbonyl-ethyl)sulfonylimine (Example 31, 0.5 g, 1.45 mmol) in ethanol (10 mL) with stirring at room temperature. After 24 hours, TLC showed the completeness of the reaction. Water was added to the reaction and the compound was extracted with chloroform and dried over sodium sulfate (50 mg). Yield is 300 mg (60%); MS (ES) m/z 345.2 (M+H)$^+$.

EXAMPLE 33

3-[[3-(4-{3-[Bis-(2-methylcarbamoyl-ethyl)-sulfamoyl]-phenylamino}-6-chloro-1,3,5]triazin-2-ylamino)-benzenesulfonyl]-(2-methylcarbamoyl-ethyl)-amino]-N-methyl-propionamide To a phosphate buffer (15 ml, PH=7) at 0° C., was added a solution of cyanuric chloride (550 mg, 2.98 mmol) in dioxane (4 ml). To the milky mixture was added a solution of 3-aminophenyl-N,N-bis-(2-methylcarbamoyl-ethyl) sulfonylimine (Example 32, 2.0 g, 5.84 mmol) in dimethylformamide (25 ml) while pH was kept at 6.5–7.2 range by addition of 1N sodium hydroxide solution. After addition, the temperature was raised to 55° C. for 2 hr. at which point HPLC analysis revealed the completion of the reaction. The mixture was diluted with water (100 ml), saturated with sodium chloride and extracted with ethyl acetate (4×150 ml). Concentration of combined extracts to a viscous oil (3.5 g) which was taken up in acetonitrile (30 ml) and left in a refrigerator overnight. The gummy precipitate was stirred with ether (20 ml) until all precipitates turned into a fine powder which was isolated through filtration. An amber solid (1.8 g, 78% yield) was obtained; m.p.>250° C. dec.; MS (ES) m/z 795.7 (M+H)$^+$.

EXAMPLE 34

4,4'-Bis-[[4,6-bis-[[3-[[bis-[3-(methylamino)-3-oxopropyl]amino]sulfonyl]phenyl]amino]-1,3,5-triazin-2-yl]amino][1,1'-biphenyl]-2,2'-disulfonic acid, disodium salt A mixture of 3-[[3-(4-{3-[bis-(2-methylcarbamoyl-ethyl)-sulfamoyl]-phenylamino}-6-chloro-[1,3,5]triazin-2-ylamino)-benzenesulfonyl]-(2-methylcarbamoyl-ethyl)-amino]-N-methyl-propionamide (Example 33, 200 mg, 0.25 mmol), 4,4'-diaminobiphenyl-2,2'-disulfonic acid, disodium salt (41 mg, 0.11 mmol) and diisopropylethylamine (50 ml, 0.28 mmol) in dimethylsulfoxide (4 ml) was heated in a sealed tube at 110° C. for 25 hr. The similar isolation procedure as above produced a white solid (40 mg, 19%); m.p.>250° C. dec.; MS (ES) m/z 930.5 (M$^{2-}$); MW 1908.1.

EXAMPLE 35

4,4'-Bis-(4,6-bis-{3-[bis-(2-methylcarbamoyl-ethyl)-sulfamoyl]-phenylamino}-[1,3,5]triazin-2-ylamino)-biphenyl-2,2'-dicarboxylic acid, disodium salt To a solution of 3-[[3-(4-{3-[bis-(2-methylcarbamoyl-ethyl)-sulfamoyl]-phenylamino}-6-chloro-[1,3,5]triazin-2-ylamino)-benzenesulfonyl]-(2-methylcarbamoyl-ethyl)-amino]-N-methyl-propionamide Example 33, 200 mg, 0.25 mmol), 4,4'-diaminobiphenyl-2,2'-dicarboxylic acid, disodium salt (37 mg, 0.12 mmol) in dimethylsulfoxide (4 ml) was added, a solution of (37 mg, 0.12 mmol) in a phosphate buffer (3 ml, PH=7). The mixture was heated at 110° C. for 24 hr. After cooling, water (100 ml) was added, and the mixture was separated on a preparative HPLC column. Yield is 60 mg (27%) of white solid; m.p.>250° C. dec.; MS (ES) m/z 894.5 (M$^{2-}$); MW 1836.0.

EXAMPLE 36

4,4'-Bis-(4,6-bis-{3-[bis-(2-carbamoyl-ethyl)-sulfamoyl]-phenylamino}-[1,3,5]triazin-2-ylamino)-biphenyl-2,2'-dicarboxylic acid dimethyl ester A mixture of 2-chloro-4,6-di[3-aminophenyl-N,N-bis(2-carbamoylethyl)-sulfonylimino]-1,3,5-triazine (Example 6, 200 mg, 0.27 mmol), 4,4'-diamino-2,2'-diphenic acid dimethyl ester² (38 mg, 0.13 mmol) and diisopropylethylamine (55 ml, 0.31 mmol) was heated at 110° C. for 30 hr. After cooling, isopropyl alcohol (50 ml) was added. The precipitate was filtered, washed with isopropyl alcohol. The dried solid (190 mg) was purified by HPLC to give a white solid (53 mg, 24% yield); m.p.>250° C. dec.; MS (ES) m/z 854.8 $(M+2H)^{2+}$; MW 1707.8.

EXAMPLE 37

3-Nitrophenyl-N,N-bis(2-hydroxypropyl) sulfonylimine

To a stirred solution of diisopropanol amine (50.0 g, 75 mmol) in water (500 ml) was added m-nitrobenzenesulfonyl chloride (57.1 g, 35 mmol). The mixture was stirred vigorously for 25 h at room temperature. The resulting suspension was filtered, the solid washed with $H_2O$ (2×400 ml), dried and re-crystallized from ethyl acetate/hexanes mixture to give the desired product as white crystals. The yield 65.8 g (88%); m.p. 114°–116° C.; $^1$H NMR (CDCl$_3$, 300 MHz) δ8.67 (d, J 5.1 Hz, 1H), 8.44 (d, 1H), 8.15 (t, J 6.0 Hz, 1H), 7.77 (m, 1H) 4.78 (s, 2H), 4.18 (m, 2H), 3.10 D, J 5.9 Hz, 4H) 1.16 (dd, 6H); MS (ES) m/z 319.5 $(M+H)^+$.

EXAMPLE 38

3-Aminophenyl-N,N-bis(2-hydroxypropyl) sulfonylimine

A solution of 3-nitrophenyl-N,N-bis(2-hydroxypropyl) sulfonylimine (Example 37, 10.0 g, 31.4 mmol) in methanol (100 ml) was hydrogenated over the palladium catalyst (10% Pd/C, 1 g) for 1.5 h. The resulting mixture was filtered through a pad of Celite, the solvent was removed and the resulting viscous oil was purified by column chromatography on Silica Gel, elution by ethyl acetate/ hexane 4:1 mixture. The desired product was obtained as light-yellow crystals. The yield 8.2 g (90.5%); NMR (CDCl$_3$, 300 MHz) δ7.28 (d, 1H), 7.13 (m, 1H), 7.09 (m, 1H), 6.86 (d, 1H) 4.20 (m, 1H), 4.13 (dd, 1H), 3.37 (dd, 1H), 3.02 (d, 2H), 2. 80 (dd, 1H); 1.16 (dd, 6H); MS (ES) m/z 289.5 $(M+H)^+$.

EXAMPLE 39

2-Chloro-4,6-bis-{3-[bis-(2-hydroxy-propyl)-sulfamoyl]-phenylamino}-[1,3,51-triazine The title compound was prepared according to the procedure of Example 33, using cyanuric chloride (160 mg, 0.87 mmol 3-aminophenyl-N,N-bis(2-hydroxypropyl) sulfonylimine (700 mg, 2.0 mmol), dioxane (3 ml), phosphate buffer (10 ml, 0.3M, pH 7), N,N-dimethylformamide (5 ml) and 1N NaOH. The product was precipitated from the cooled reaction mixture with water as a viscous amber-yellow oil, centrifuged, washed with water and dried on the high vacuum to give 640 mg (93%) of the chlorotriazine. m.p.>250° C. dec; MS (ES) m/z 687.7, 689.7 $(M+H)^+$.

EXAMPLE 40

4,4'-Bis-(4,6-bis-{3-[bis-(2-hydroxy-propyl)-sulfamoyl]-phenylamino}-[1,3,5]-triazin-2-ylamino) biphenyl-2,2'-disulfonic acid, disodium salt A mixture of 2-chloro-4,6-bis-{3-[bis-(2-hydroxy-propyl)-sulfamoyl]-phenylamino}-[1,3,5]-triazine (Example 39, 300 mg, 0.44 mmol), 4,4'-diaminobiphenyl-2,2'-disulfonic acid, disodium salt (77 mg, 0.2 mmol), 2 ml of DMSO, 2 ml of the phosphate buffer (1N, pH 7) and 0.25 ml of 1N NaOH was exposed to a microwave heating (PROLABO unit, monomode regimen) at 110° C. for 2 h. After cooling the reaction mixture without workup was submitted to preparative HPLC in water/acetonitrile system on YMC Prodigy C18 polymer column. The product was obtained as colorless solid (170 mg, 50.2%); m.p.>250° C. dec; MS (ES) m/z 822.3 $(M-2H)^{2-}$; MW 1691.9 (MW+2Na)

EXAMPLE 41

4,4'-Bis-(4,6-bis-{3-[bis-(2-hydroxy-propyl)-sulfamoyl]-phenylamino}-[1,3,5-triazin-2-ylamino) biphenyl-2,2'-dicarboxylic acid, disodium salt A mixture of 2-chloro-4,6-bis-{3-[bis-(2-hydroxy-propyl)-sulfamoyl]-phenylamino}-[1,3,5]-triazine (Example 39, 178 mg, 0.25 mmol), 4,4'-diamino-2,2'-diphenic acid, dihydrochloride (35 mg, 0.11 mmol), 3 ml of DMSO, 0.5 ml of the phosphate buffer (1N, pH 7) and 0.5 ml of 1N NaOH was heated in the oven in a sealed tube for 18 h, then without a workup submitted for the prep. HPLC to give 90 mg (50.5%) of the desired product. m.p.>250° C. dec; MS (ES) m/z 788.1 $(M+2H)^{2+}$; MW 1619.8 (MW+2Na)

EXAMPLE 42

2-Chloro-4,6-bis-{3-[bis-carbamoylmethyl-1-sulfamoyl]-phenylamino}-[1,3,5]-triazine The title compound was prepared according to the procedure of Example 33, using cyanuric chloride (0.42 g, 2.27 mmol), 3-aminophenyl-N,N-bis-carbamoylmethyl-sulfonylimine (CL 55675, 1.43 g, 5.0 mmol), dioxane (2 ml), phosphate buffer (10 ml, 0.3M, pH 7), N,N-dimethylformamide (4 ml) and 1N NaOH. The reaction mixture was heterogeneous during the whole procedure. The formed pink precipitate was centrifuged, washed several times with water, redissolved in a minimal amount of DMF and re-precipitated by water. The final separation and drying gave 0.7 g (45.1%) of the desired product; m.p.>250° C. dec; MS (ES) m/z 683.7, 685.7 $(M+H)^+$.

EXAMPLE 43

4',4-Bis-{4,6-bis-[3-(bis-carbamoylmethyl-1-sulfamoyl)-phenylamino]-[1,3,5]triazin-2-ylamino}-biphenyl-2,2'-disulfonic acid, disodium salt The title compound was prepared according to the procedure of Example 40, using 2-chloro-4,6-bis-{3-[bis-carbamoylmethyl-1-sulfamoyl]-phenylamino}-[1,3,5]-triazine (Example 42, 500 mg, 0.73 mmol), 4,4'-diaminobiphenyl-2,2'-disulfonic acid, disodium salt (114 mg, 0.29 mmol), 2.5 ml of DMSO, 2.5 ml of the phosphate buffer (1N, pH 7) and 1.0 ml of 1N NaOH. The microwave heating (PROLABO unit, monomode regimen) was continued for 1 h at 105° C. The resulting mixture was submitted for the prep. HPLC, which gave 50 mg (10.2%) of the product as a pink solid; m.p.>250° C. dec; MS (ES) m/z 818.2 $(M-2H)^{2-}$; MW 1683.7 (MW+2Na)

EXAMPLE 44

4',4-Bis-{4,6-bis-[3-(bis-carbamoylmethyl-1-sulfamoyl)-phenylamino]-[1,3,5]triazin-2-ylamino}-biphenyl-2,2'-dicarboxylic acid, disodium salt The tide compound was prepared according to the procedure of Example 40 using 2-chloro-4,6-bis-{3-[biscarbamoylmethyl-1-sulfamoyl]-phenylamino}-[1,3,5]-triazine (Example 42, 500 mg, 0.73 mmol), 4,4'-diamino-2, 2'-diphenic acid, dihydrochloride (100 mg, 0.29 mmol), 2.5 ml of DMSO, 2.5 ml of the phosphate buffer (1N, pH 7) and 1.0 ml of 1N NaOH. The microwave heating (PROLABO unit, monomode regimen) was continued for 1 h at 105° C. The resulting mixture was submitted for the prep. HPLC, which gave 20 mg (4.3%) of the product as a pink solid; m.p.>250° C. dec; MS (ES) m/z 784.0 $(M+2H)^{2+}$; MW 1619.8 (MW+2Na).

EXAMPLE 45

1-(3-Nitro-benzenesulfonyl)piperidine-3,5-dicarboxylic acid

A solution of 3,5-pyridinedicarboxylic acid (3.34 g, 20 mmol) in 50 ml of water and 10 ml of conc. ammonium hydroxide was hydrogenated in Parr apparatus at 22 Psi over 1 g of ruthenium catalyst (5% ruthenium on alumina powder) for 48 h. After filtration of the catalyst and solvent removing the crude 3,5-piperidinedicarboxylic acid was dissolved in 60 ml of 1N NaOH and treated with 6.6 g (30 mmol) of m-nitrobenzenesulfochloride. The reaction mixture was stirred at room temperature and pH maintained at 9.5 by addition of 1N NaOH until it stopped to drop down. The reaction mixture was stirred for an additional 1.5 h, the formed precipitate was filtered, and the filtrate was acidified by conc. HCl to pH 2–3. The formed white precipitate was filtered, washed with water and dried in high vacuum overnight to give 5.3 g (74%) of the desired product. $^1$H NMR (DMSO-$d_6$, 300 MHz) δ8.55 (d, 1H), 8.40(s, 1H), 8.15 (d, 1H), 7.95 (t, 1H) 3.14 (m, 4H), 1.65 (m, 2H), 1.45 (m, 2H); MS (ES) m/z 359 $(M+H)^+$.

EXAMPLE 46

1-(3-Nitro-benzenesulfonyl)piperidine-3,5-dicarboxylic acid dimethyl ester

A suspension of 1-(3-nitro-benzenesulfonyl)piperidine-3,5-dicarboxylic acid (Example 45, 3.6 g, 10 mmol) in THF (200 ml) was treated at 0° C. by the excess of diazomethane and stirred at that temperature until the suspension turned into clear bright-yellow solution. The reaction mixture was warmed to the room temperature, filtered, evaporated and purified by column chromatography on Silica Gel, elution by chloroform, to give 2.5 g (64%) of the desired products colorless crystals. $^1$H NMR (CDCl$_3$, 300 MHz) δ8.65 (s, 1H), 8.49(d, 1H), 8.11 (d, 1H), 7.81 (t, 1H) 3.73 (s, 6H), 3.40 (m, 4H), 2.95 (m, 2H), 2.05 (t, 2H); MS (ES) m/z 387.2 $(M+H)^+$.

EXAMPLE 47

1-(3-Nitro-benzenesulfonyl)piperidine-3,5-dicarboxylic acid diamide

A solution of 1-(3-nitro-benzenesulfonyl)piperidine-3,5-dicarboxylic acid dimethyl ester (Example 46, 2.5 g, 6.5 mmol) in 200 ml of methanol, saturated by ammonia at 0° C., was sealed and left at the room temperature for 7 days. The resulting yellow solution was concentrated to the volume 100 ml, the formed precipitate filtered, washed with methanol and dried to give 1.8 g (77.7%) of the product as light-creamy crystals. MS (ES) m/z 357.1 $(M+H)^+$.

EXAMPLE 48

1-(3-Amino-benzenesulfonyl)piperidine-3,5-dicarboxylic acid

A solution of 1-(3-nitro-benzenesulfonyl)piperidine-3,5-dicarboxylic acid (Example 45, 2.5 g, 4.2 mmol) in 150 ml of methanol was hydrogenated in Parr apparatus at 25 Psi over 0.15 g of the palladium catalyst (10% palladium on carbon) for 1 h. Filtration of the catalyst and solvent removing gave 1.8 g (79%) of the desired product as a white solid. MS (ES) m/z 329.1 $(M+H)^+$.

EXAMPLE 49

1-(3-Amino-benzenesulfonyl)piperidine-3,5-dicarboxylic acid diamide

A solution of 1-(3-nitro-benzenesulfonyl)piperidine-3,5-dicarboxylic acid diamide (Example 47, 1.5 g, 4.2 mmol) in 300 ml of methanol was hydrogenated in Parr apparatus at 25 Psi over 0.1 g of the palladium catalyst (10% palladium on carbon) for 1.5 h. Filtration of the catalyst and solvent removing gave 1.26 g (92%) of the desired product as a light-gray solid. MS (ES) m/z 327.1 $(M+H)^+$.

EXAMPLE 50

2-Chloro-4,6-bis-[3-(3,5-dicarbamoyl-piperidine-1-sulfonyl)-phenylamino]-[1,3,5]triazine A solution of cyanuric chloride (280 mg, 1.5 mmol) in dioxane (5 ml) was added with stirring to phosphate buffer (10 ml, 0.3M, pH 7) at 0°–2° C. To the resulting suspension was added dropwise a solution of 1-(3-amino-benzenesulfonyl)piperidine-3,5-dicarboxylic acid diamide (Example 49, 1.0 g, 3.1 mmol) in N,N-dimethylformamide (5 ml) and the pH maintained at 6.5–7.2 by addition of 1N NaOH. After completion of the addition, the reaction mixture was warmed up to 50°–55° C. and stirred at that temperature for 2 h (until HPLC showed the completion of the reaction), then cooled to the room temperature, diluted with water, the product precipitate filtered, washed with cold water (10 ml), acetone (5 ml) and dried under vacuum at 20° C. to give 845 mg (74.2%) of the desired product; m.p.>250° C. dec; MS (ES) m/z 765.0 (M+H), MW 764.2.

EXAMPLE 51

2-Chloro-4,6-bis-[3-(3,5-dicarboxyl-piperidine-1-sulfonyl)-phenylamino]-[1,3,5]triazine The title compound was prepared according to the procedure of Example using cyanuric chloride (280 mg, 1.5 mmol), 1-(3-amino-benzenesulfonyl)piperidine-3,5-dicarboxylic acid (Example 48, 1.0 g, 3.1 mmol), dioxane (3 ml), phosphate buffer (10 ml, 0.3M, pH 7), N,N-dimethylformamide (5 ml) and 1N NaOH. After completion of the reaction the mixture was cooled to the room temperature, diluted with water, acidified by HCl to pH 5, the product precipitate filtered, washed with cold water (10 ml), and dried under vacuum at 20° C. to give 845 mg (74.2%) of the desired product; m.p.>250° C. dec; MS (ES) m/z 769.0 (M+H), MW 767.8.

EXAMPLE 52

(E)-2,2'-(1,2-Ethenediyl)bis[5-[[4,6-bis[[3-[[3,5-bis (aminocarbonyl)-1-piperedinyl]sulfonyl]phenyl] amino]-1,3,5-triazin-2-yl]amino]benzenesulfonic acid], disodium salt A suspension of 4,4'-diaminostilbene-2,2'-disulfonic acid, disodium salt (0.41 g, 0.1 mmol) and 2-chloro-4,6-bis-[3-(3,5-dicarbamoyl-piperidine-1-sulfonyl)-phenylamino]-[1, 3,5]triazine (Example 50) (1.62 g, 0.21 mmol) in sulfolane (3 ml) and dimethylformamide (5 ml) in the presence of diisopropylethylamine (0.08 ml) was warmed in a sealed thick-walled glass tube to 115° C. Warming was continued for 40 hours. Once the reaction was complete as determined by analytical HPLC (or TLC), the mixture was cooled to 30° C., 1N NaOH (0.5 ml) was added and the product precipitated by the addition of propan-2-ol (50 ml). The precipitate was filtered, washed with acetone (30 ml) and redissolved in a minimum volume of water and re-precipitated by the addition of ethanol. The precipitate after filtration was washed with ether (30 ml) and dried under vacuum at 50° C. Yield 1.59 g (85%); MS(ES) m/z 911.7 (M−2H)$^{2-}$; MW 1869.9(2Na).

EXAMPLE 53

4',4-Bis-{4,6-bis-[3-(3,5-dicarbamoyl-piperidine-1-sulfonyl)-phenylamino]-[1,3,5]triazin-2-ylamino}-biphenyl-2,2'-disulfonic acid, disodium salt The title compound was prepared according to the procedure of Example using 4,4'-diaminobiphenyl-2,2'-disulfonic acid, disodium salt (40 mg, 0.1 mmol) and 2-chloro-4,6-bis-[3-(3,5-dicarbamoyl-piperidine-1-sulfonyl)-phenylamino]-[1,3,5]triazine (Example 50) (176 mg, 0.23 mmol) in 60 ml DMSO-sulfolane (1:3, v/v) and diisopropylethylamine (0.08 ml). The product was obtained as a creamy solid (153 mg, 83%); m.p.>250° C. dec; MS(ES) (m/z) 898.3 (M−2H)$^{2-}$; MW 1843.9 (M+2Na).

EXAMPLE 54

1,2',1''',1'''-[(2,2'-disulfo[1,1'-biphenyl]-4,4'-diyl)-bis[imino-1,3,5-triazine-6,2,4-triylbis(imino-3,1-phenylenesulfonyl)]tetrakis[3,5-piperidinedicarboxylic acid The title compound was prepared according to the procedure of Example using 4,4'-diaminobiphenyl-2,2'-disulfonic acid, disodium salt (270 mg, 0.68 mmol) and 2-chloro-4,6-bis-[3-(3,5-dicarboxyl-piperidine-1-sulfonyl)-phenylamino]-[1,3,5]triazine (Example 51) (1.1 g, 1.43 mmol) in 60 ml DMSO-sulfolane (1:1, v/v) and diisopropylethylamine (1.2 ml). The product after precipitation by the addition of propan-2-ol was filtered, washed with acetone (30 ml), dried, redissolved in a minimum volume of water and re-precipitated by acidifying (HCl) to pH 1–2. The desired product was obtained as a creamy solid (1.0 g, 80%); m.p.>250° C. dec; MS(ES) (m/z) 902.2 (M−2H)$^{2-}$; MW 1807.8.

EXAMPLE 55

3-Nitrophenyl-N,N-bis(2-hydroxyethyl)sulfonylimine

Diethanolamine (Aldrich; 25.0 g, .238 Mol) was dissolved in 55 mL 9:1 methylene chloride/THF and chilled to 5° C. A solution of 3-nitrobenzenesulfonyl chloride (Aldrich; 25.0 g, .113 Mol) in 35 mL THF was added over 10 minutes. Ice bath was removed; reaction stirred for an additional 30 minutes. Then the solvents were stripped off and the residue was partitioned between water (100 mL) and ethyl acetate (150 mL). The aqueous layer was extracted with three 25 mL portions of ethyl acetate. The combined organic layer was dried over MgSO$_4$, filtered through a pad of silica and concentrated in vacuo. The product crystallizes out during this evaporation and is filtered, giving 17.4 g (53.2%) of white needles. m.p. 99°–100° C. MS(ES) m/z 291.2 (M+H)$^{1+}$.

EXAMPLE 56

3-Aminophenyl-N,N-bis(2-hydroxyethyl)sulfonylimine

The nitro compound (Example 55, 17.2 g, 59.3 mmol) and 1.72 g of 10% Pd/C were suspended in 170 mL ethanol. The mixture was reduced under 40 psi hydrogen for two hours. The catalyst was filtered off and the clear colorless filtrate was evaporated to dryness, giving 15.4 g (98% yield) of the corresponding amino compound. MS(ES) m/z 261.0 (M+H)$^{1+}$

EXAMPLE 57

4,4'-Bis-(4,6-bis-{3-[bis-(2-hydroxyethyl)-sulfamoyl]-phenylamino}-[1,3,5-triazin-2-ylamino)biphenyl-2,2'-dicarboxylic acid, disodium salt A solution of trichlorotriazine (1.55 g; 8.4 mmol) in 20 mL dioxane was added to 60 mL of pH 7 buffer at 0° C. To the resulting fine suspension was added dropwise a solution of 4,4'-diamino-2,2'-diphenic acid (P.R. 232–10; 1.55 g, 4.0 mMol) in 10 mL water, keeping the pH 6.5–7.1 with 1N NaOH. Once the addition is complete and the pH has stabilized, the reaction mixture is allowed to warm to ambient temperature. A solution of the diethanolsulfonamide (2.6 g, 10 mMol) in 20 mL dioxane and solid sodium bicarbonate (0.84 g, 10 mMol) are added and the resulting mixture is heated at reflux (92° C.) for two days. The clear yellow solution is cooled and the dioxane is stripped off. The product precipitates out of aqueous solution and is collected by vacuum filtration giving 3.16 g of the desired compound, approximately 65% pure by HPLC as a white amorphous solid. m.p.>250° C. dec; MS(ES) (m/z) 732.5 (M+2H)$^{2+}$; MW 1507.6 (M+2Na).

EXAMPLE 58

3-Aminophenyl-N,N-bis(3-hydroxypropyl)sulfonylimine

A solution of 3-aminophenyl-N,N-bis(2-methoxycarbonyl-ethyl)sulfonylimine (Example 31, 150 mg, 0.4 mmol) in THF (15 mL) was added to a solution of LiAlH$_4$ (3 mL, 1M in THF) with stirring under nitrogen at 0° C. After 45 minutes, TLC shows the completeness of the reaction. A solution of ammonium chloride (15 mL, 1M) was added to the solution and a white precipitate formed and solution turned yellow. The yellowish solution was decanted and the white precipitate was washed with ethyl acetate. The organics were dried over sodium sulfate and rotary evaporated to give a desired product as a yellow oil. Yield is 110 mg (95.6%), (m/z): MH 289.2.

EXAMPLE 59

4,4'-Bis[4,6-di[3-aminophenyl-N,N-bis(3-hydroxypropyl)-sulfonylimino]-1,3,5-triazin-2-ylamino]-biphenyl-2,2'-disulfonic acid, disodium salt The title compound was prepared using the general conditions of Example 1, where cyanuric chloride (92 mg, 0.50 mmol) was reacted with 4,4'-diaminobiphenyl-2,2'-disulfonic acid, disodium salt (93 mg, 0.24 mmol) for 1 hour, and then with 3-aminophenyl-N,N-bis(3-hydroxypropyl)sulfonylimine (708 mg, 2.5 mmol) (Example 58). Once the reaction was complete as determined by analytical HPLC (or TLC), the mixture was cooled to 20° C., and the product precipitated by addition of propan-2-ol (40 ml), washed on filter with cold propan-2-ol (15 ml), and dried under vacuum at 40° C. Two portions of a solution of crude product (about 0.35 g) in deionised water (200 ml) were purified separately by preparative RP-HPLC. Fractions containing the desired product were combined, organic solvents evaporated under vacuum (10 mm Hg) at 30° C., and the product concentrated, desalted and isolated via octadecyl (C18) cartridge (900 mg, obtained from Burdick & Jackson). The cartridge was washed with water (40 ml) and the product reextracted with methanol (60 ml). Evaporation of the methanol gives 162 mg (40%) of the desired product; m.p.>300° C. dec; MS(ES) (m/z): $M^{-2}$ 822.4; MW 1690.8.

Effects of the compounds in viral yield reduction assays

The compounds were tested for biological activity using viral yield reduction assays. Host cells (indicated as HF for human foreskin fibroblasts and as vero, the commonly used African green monkey cell line, in Tables 1 and 1a) were plated at $4 \times 10^4$ cells/well in cell growth medium with 2% fetal bovine serum or 2% calf serum in 96-well plates (0.1 ml/well) and incubated overnight. The compounds were added to individual wells to give final concentrations ranging from 50 to 0.1 µg/ml in two-fold concentration steps. After 1 hour, virus was added, and the incubation was continued for 4 days with RSV or CMV and for 2 days with HSV. At the end of the experiment, the amount of virus growth was quantitated and the yield reduction at various concentrations of compound was calculated. This allows estimation of the concentration of compound giving 50% reduction in virus growth ($IC_{50}$).

Tables 1 and 1a (a summary of biological activity) summarizes the activity of the compounds in viral yield reduction assays.

Effects of the compounds in viral plague reduction assays

The compounds were tested for the ability to inhibit viral plaque formation. Host cells, as indicated in Tables 1, 1a and 2, are plated at $10^6$ cells/well in 6-well plates and incubated overnight. One of two formats was then followed. In the normal (pretreatment) format, the cell growth medium was replaced with 1 ml of medium containing compound at a given concentration. Virus (~100 plaque-forming units in 40 µl) was added after 1 hour. After a further hour, the medium was replaced with 4 ml of medium containing compound at the concentration being tested. The cells were then incubated for a time sufficient to allow the formation of viral plaques. Occasionally, compound was added only after the infection had begun (posttreatment). In this case, the growth medium was replaced with 1 ml of medium containing approximately 100 plaque-forming units. After 1 hour, this was replaced with 2 ml of growth medium. After a further period specified in Table 2, a further 2 ml containing compound was added. In either case, the number of plaques in a series of wells containing a range of compound concentrations was compared to the number in a well with no compound, and the $IC_{50}$ was determined by graphing the data and identifying the compound concentration giving a 50% reduction in viral plaque number.

Tables 1, 1a and 2 summarize antiviral activity in plaque assays. It can be seen that the title compounds of Examples 1 and 4 are active against all RSV strains tested at approximately 0.1–0.7 µg/ml. Activity can also be seen with certain members of other virus families (in the range 3–20 µg/ml). These results confirm and extend the data from yield reduction assays indicating that these compounds are potent and specific inhibitors of RSV.

TABLE 1

In vitro activity of the compounds against Respiratory Syncytial Virus, Cytomegalovirus, and Herpes Simplex Virus

| Compound of Example | IC50 µG/mL IN GROWTH INHIBITION | | | | | IC50 µG/mL IN PLAQUE ASSAY | | |
|---|---|---|---|---|---|---|---|---|
| | RSV/ HF | RSV/ VERO | CMV/ HF | HSV/ HF | HSV/ VERO | RSV/ VERO | CMV/ HF | HSV/ VERO |
| 11 | 10 | 10 | >50 | | | | | |
| 9 | <3 | 0.4 | | | | 0.3 | 10 | |
| 10 | <3 | 0.7 | | | | | | |
| 6 | >50 | >50 | >50 | | | | | |
| 1 | 0.3 | 0.5 | | | | 0.3 | 7 | 8 |
| 4 | 0.1 | 0.1 | 35 | 20 | 35 | 0.1 | >30 | 35 |
| 5 | | 0.4 | | | | | | 8 |
| 7 | 0.7 | 1 | | | | 0.8 | 10 | |
| 8 | >50 | >50 | >50 | | | | | |
| 12 | | | | | | 8 | 10 | |
| 13 | 8 | 8 | 20 | 10 | 30 | | | |
| 15 | 7 | >8.3 | 2 | | | | 1 | |
| 16 | 5 | ~8.3 | 3 | | | | 3 | |
| 17 | >50 | >50 | | | >50 | | | |
| 19 | 2 | 3 | 12 | 30 | ~50 | | | |
| 20 | 0.5 | | | | 40 | | | |
| 22 | 0.15 | 0.25 | 4 | | | | 2 | |
| 23 | | | | | | 8 | 20 | |
| 24 | | 50 | | | | | | |
| 25 | | 30 | | | | | | |

Table 1. Fifty percent inhibitory concentrations for growth inhibition (yield reduction) and for plaque formation were determined as described in the text. The virus strains used were RSV (A2), CMV (Ad169), HSV1 (Patton). The host cells used were human foreskin fibroblasts (HF) and vero cells.

TABLE 1a

In vitro activity of the compounds against Respiratory Syncytial Virus, Cytomegalovirus and Herpes Simplex Virus

| Compound of Example | Antiviral IC50 μg/ml | | | | Effect on cells @ μg/ml indicated | |
|---|---|---|---|---|---|---|
| | RSV/ HF | RSV/ Vero | CMV /HF | HSV Vero | HF | Vero |
| Example 52 | 1.5 | 1.5 | | | L @ 37 | |
| Example 53 | 2 | 7 | | >50 | N @ 75 | N @ 75 |
| Example 54 | 35 | >50 | >50 | | N @ 75 | |
| Example 57 | 1.5 | | 4 | 30 | | N @ 75 |
| Example 34 | 1.2 | >50 | >50 | | N @ 75 | L @ 75 |
| Example 35 | 6 | >50 | >50 | | | N @ 75 |
| Example 43 | 0.1 | | 2.5 | 6 | N @ 75 | N @ 75 |
| Example 44 | 0.6 | | 1.5 | 15 | L @ 75 | L @ 75 |
| Example 40 | 0.2 | | 4 | 20 | N @ 75 | N @ 75 |
| Example 41 | 2 | | 8 | >50 | | |
| Example 30 | 0.35 | | 40 | >50 | N @ 75 | |
| Example 59 | 0.5 | | 4 | 20 | | |

Fifty percent inhibitory concentration for growth inhibition (yield reduction) and for plaque formation were determined as described in the text. The virus strains used were RSV (A2), CMV (Ad169), and HSV1 (Patton). The host cells used were human foreskin fibroblasts (HF) and vero cells.
N, no effect on the appearance of the alcohol-fixed and crystal violet-stained cell monolayer at the indicated compound concentration.
L, lightening of the intensity of staining (compared to controls) of the alcohol-fixed and crystal violet-stained cell monolayer at the indicated compound concentration but not at half that concentration.

TABLE 2

Effect of Examples 1 and 4 on viral plaque formation

| Virus Strain (Cell) | IC50 (μG/mL) | | | | |
|---|---|---|---|---|---|
| | Example 1 | | | Example 4 | |
| | | Post (hours) | | | Post (hours) |
| | Pre | 2 | 24 | Pre | 2 |
| RSV (VERO) | | | | | |
| A2 | 0.3 | 0.3 | 0.4 | 0.1 | 0.28 |
| LONG | 0.2 | | | | 0.21 |
| 3A | 0.5 | | | | 0.15 |
| 9320 | 0.2 | | | | 0.18 |
| 2B | 0.1 | | | | 0.08 |
| RSS2 | | | | | 0.20 |
| 18736 | | | | | 0.06 |
| RSV (HF) | | | | | |
| A2 | 0.4 | <3 | | | |
| RSV (SKNSH) | | | | | |
| A2 | 0.4 | | | | |
| RSV (MDBK) | | | | | |
| A2 | 0.4 | | | | |
| HPIV3 (VERO) | | | | | |
| WASH. | 20 | | | | |
| FLU (MDCK) | | | | | |
| A1/FM/1/47 | >50 | | | | |
| A2/HK/8/68 | >50 | | | | |
| A2/JPN/305/57 | >50 | | | | |
| A/Texas/36/91 | 5 | | | | |
| A/Beij/32/92 | >20 | | | | |
| B/Pana/45/90 | >20 | | | | |
| HCMV (HF) | | | | | |
| Ad169 | 15 | | | >30 | |
| HSV1 (VERO) | | | | | |
| Patton | | | | 35 | |

TABLE 2-continued

Effect of Examples 1 and 4 on viral plaque formation

| Virus Strain (Cell) | IC50 (μG/mL) | | | | |
|---|---|---|---|---|---|
| | Example 1 | | | Example 4 | |
| | | Post (hours) | | | Post (hours) |
| | Pre | 2 | 24 | Pre | 2 |
| HSV2 (VERO) | | | | | |
| 333 | 3 | | | | |
| 12 | >10 | | | | |
| MS | 5 | | | | |

In the pretreatment protocol, confluent cells in 6-well dishes were treated with various concentrations of compound for 1 h. Virus (~100 pfu) was added in a small volume and plaques were counted after incubation (RSV, CMV, and HPIV3 (human parainfluenza virus type 3, strain Washington), 5–8 days; influenza and herpes simplex virus, 2 days). For posttreatment, cells were first infected for 1 h and the medium (containing unabsorbed virus) was replaced. Medium containing compound at various concentrations was added at 2 h or 24 h after the end of the infection period. Cells used included vero (African green monkey cells), HF (human foreskin fibroblast cells), SKNSH (human neuroblastoma cells), MDBK (Madin-Darby bovine kidney cells), and MDCK (Madin-Darby canine kidney cells).

Mechanism of action

The time in the virus life-cycle when Example 1 exerts its effect was determined to increase understanding of the mechanism of action. This was accomplished by adding and removing the compound at various times relative to infection and assessing the effect on viral protein synthesis. Vero cells were infected on ice for 1 hour, unadsorbed virus was removed, and then the infected cells were incubated at 37° C. for 18 hours (virus adsorption will occur on ice, but fusion will not proceed until the temperature is raised to 18° C. or above). After the 18 hour incubation at 37° C. (when the bulk of ongoing protein synthesis was directed by viral RNAs), $^{35}$S-methionine was added for 2 hours, the cells were lysed, and the labeled proteins were analyzed on SDS-PAGE gels. The viral N, P, and M proteins were then evident. If the compound of Example 1 was added at 10 μg/ml immediately after virus adsorption and before raising the incubation temperature to 37° C., viral protein synthesis was fully prevented. However, when the compound of Example 1 was added even after only 5 minutes incubation at 37° C., viral protein production was unimpeded. Therefore, the process inhibited was the fusion process or some closely succeeding step which is required for later viral gene expression.

It is known that RSV-infected cells in close contact will fuse to form syncytia and that this process is dependent only on the viral F, SH, and G proteins (Heminway B. R., Yu Y., Tanaka Y., Perrine K. G., Gustafson E., Bernstein J. M., Galinski M. S. 1994. Analysis of respiratory syncytial virus F, G, and SH proteins in cell fusion. Virology 200;801–805). Syncytium formation should not involve viral functions, such as uncoating or transcription, which normally succeed it and which are required for later viral gene expression.

To determine if the compounds of this invention inhibit fusion or a succeeding step, they were tested for the ability to prevent syncytium formation in cells previously infected with RSV. This was done by infecting vero cells at a multiplicity of infection of 3 for 1 hour, then replacing the original medium with fresh medium. After 6 hours incubation, compound was added. After 24 and 48 hours, the infected cells were examined under the microscope to determine the extent of syncytium formation. Differences in the extent of syncytium formation due to the presence of compound were easily recognized and the compounds were easily ranked in terms of potency in this assay. The actual IC50's as judged by this method are approximate. They were 0.3 and 0.05 μg/ml for compounds 16 and 17, respectively. The ability of these compounds to inhibit syncytium formation demonstrates that they act at the fusion step of the virus life-cycle.

Compounds of Examples 1 and 4 prevent RSV growth in vivo

RSV infection of cotton rats followed by drug delivery by small particle aerosol (SPA) was used to assess a compound's in vivo anti-RSV potential. (Gilbert B. E., Wyde P. R., Wilson S. Z., and Meyerson L. R. 1993. SP-303 small particle aerosol treatment of influenza A virus infection in mice and respiratory syncytial virus infection in cotton rats. Antiviral Research 21;37–45.)

The compounds of the present invention were tested in this system to determine if they can inhibit growth of RSV in cotton rats. In experiment 1 (see Table 3), animals were infected intranasally with RSV A2 (day 0), which results in a respiratory infection. Ribavirin was used at 60 mg/ml in water in the aerosolizing chamber and was administered for 2 hours twice a day on days 1, 2, and 3 after infection. Compound 16 was used at 4.5 mg/ml in 25 mM NaHCO$_3$ in the aerosolizing chamber and was administered for 4 hours before infection and for 8 hours on each of days 1, 2, and 3. The placebo was water used according to the same regimen as compound 16. The animals were sacrificed on day 4, the lungs were lavaged, and the titers of RSV in the lavages determined. In experiment 2, infected untreated animals and animals exposed to an aerosol of 25 mM NaHCO3 served as controls. The compounds of Examples 1 and 4 were made up at 5 mg/ml in 25 mM NaHCO3. One group was treated with the compound of Example 1 for 4 hours before infection on day 0 and for 8 hours on each of days 1, 2, and 3 (prophylactic regimen). One group was treated with the compound of Example 1 for 8 hours only on each of days 1, 2, and 3 (therapeutic regimen). A final group was treated with the compound of Example 4 for 8 hours on each of days 1, 2, and 3 (therapeutic regimen). On day 4, all animals were sacrificed, the lungs were lavaged, and the titers of RSV in the lavages were determined. In experiment 3, the placebo was water delivered intranasally once a day. The compound of Example 4 was tested by intranasal delivery by dosing before inoculation and 1 day thereafter (days 0 and 1), by dosing before inoculation and on days 1–3, and by dosing only after inoculation on days 1–3. The compound was also tested by dosing intraperitoneally. On day 4, all animals were sacrificed, their lungs were lavaged, and the titers of RSV in the lavages were determined. This was done by determining the dilution end-point which produces cytopathic effect (CPE) in vero cells and also by plaque assay on vero cells. The lungs were also homogenized and the titers of virus in the lungs were determined by centrifuging out particulate material (1000×g, 10 minutes) and using dilutions of the supernatants in plaque assays. It can be seen that the compounds of Examples 1 and 4 inhibit RSV in vivo.

TABLE 3

Efficacy of Examples 1 and 4 against Respiratory Syncitial Virus in Cotton Rats

| EXPT | Treatment | Regimen | N | Sample/Assay | Mean titer log10/g lung | SD | Fold red. log10 |
|---|---|---|---|---|---|---|---|
| 1 | H2O aerosol | 2 × 2 h/d d 1,2,3 | 5 | Lavage/CPE | 4.1 | 0.27 | |
| | Ribavirin aerosol | 60 mg/ml 2 × 2 h/d d 1,2,3 | 4 | Lavage/CPE | 3.3 | 0 | 0.8 |
| | Example 1 aerosol | 4.5 mg/ml 4 h d 0 8 h d 1,2,3 | 5 | Lavage/CPE | 2.8 | 0.35 | 1.3 |
| 2 | Untreated | | 4 | Lavage/CPE | 3.68 | 0.48 | |
| | Placebo aerosol | 4 h d 0 8 h d 1,2,3 | 4 | Lavage/CPE | 3.43 | 0.25 | 0.25 |
| | Example 1 aerosol | 5 mg/ml 4 h d 0 8 h d 1,2,3 | 4 | Lavage/CPE | 1.73 | 1.15 | 1.95 |
| | Example 1 aerosol | 5 mg/ml 8 h d 1,2,3 | 4 | Lavage/CPE | 3.43 | 0.25 | 0.25 |
| | Example 4 aerosol | 5 mg/ml 8 h d 1,2,3 | 4 | Lavage/CPE | 2.05 | 0.5 | 1.63 |
| 3 | H2O i.n. | d 0,1,2,3 | 4 | Lavage/CPE | 4.18 | 0.25 | |
| | | | | Lavage/Plaque | 4.29 | 0.13 | |
| | | | | Lung/Plaque | 4.55 | 0.24 | |
| | Example 4 i.n. | d 0 15 mg/k d 1 30 mg/k | 4 | Lavage/CPE | 1.66 | 0.25 | 2.52 |
| | | | | Lavage/Plaque | 2.26 | 0.11 | 2.03 |
| | | | | Lung/Plaque | 2.32 | 0.23 | 2.23 |
| | Example 4 i.n. | d 0 15 mg/k d 1,2,3 30 mg/k | 4 | Lavage/CPE | 2.05 | 0.87 | 2.13 |
| | | | | Lavage/Plaque | 2.25 | 0 | 2.04 |
| | | | | Lung/Plaque | 2.25 | 0 | 2.3 |
| | Example 4 i.n. | 30 mg/k d 1,2,3 | 4 | Lavage/CPE | 1.67 | 0.48 | 2.51 |
| | | | | Lavage/Plaque | 3.09 | 0.65 | 1.2 |
| | | | | Lung/Plaque | 3.37 | 1.09 | 1.18 |
| | Example 4 i.p. | 30 mg/k d 1,2,3 | 4 | Lavage/CPE | 4.18 | 0.25 | 0 |
| | | | | Lavage/Plaque | 4.1 | 0.22 | 0.09 |
| | | | | Lung/Plaque | 3.92 | 0.97 | 0.26 |

What is claimed:

1. A compound having the structure:

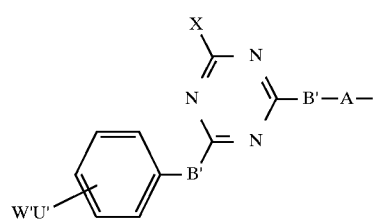

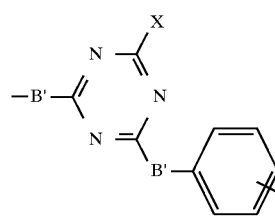

wherein:

A is a moiety selected from the group consisting of

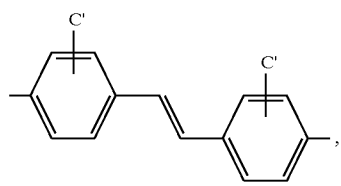

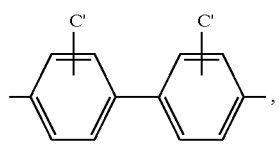

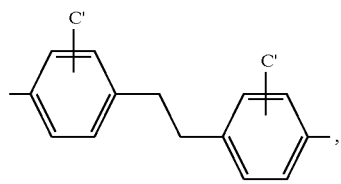

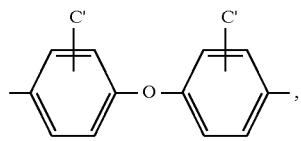

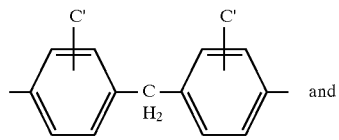

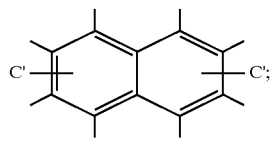

C' is selected from —SO$_3$H, —OSO$_3$H, —OH, or —COOH;

B' is selected from —NH, —NR$^1$ or O;

R$^1$ is selected from H, (C$_1$–C$_6$)lower alkyl straight or branched wherein the carbon atoms may be optionally substituted with Cl, Br, F, OH or CN;

X is selected from Cl, F or the moiety

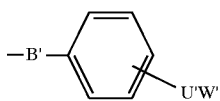

where

U' is selected from the group of —SO$_2$, —CO, —NC(O), or —NC(S);

W' is selected from the moieties:

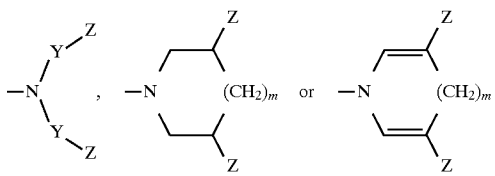

Y is —(CH$_2$)$_n$—;

n is 0 to 6;

m is 0 to 2;

Z is selected from H, CH$_3$, CF$_3$, —CH$_2$—(halogen), where halogen is Cl, Br, F or I, —CH$_2$OH, —COOH, —COO(C$_1$–C$_6$)lower alkyl straight or branched, —CONR$^2$R$^2$, CN or

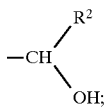

R$^2$, in each occurrence, is independently selected from H or (C$_1$–C$_6$)lower alkyl; or a pharmaceutically acceptable salt or ester thereof.

2. A compound of claim 1 wherein A is the moiety:

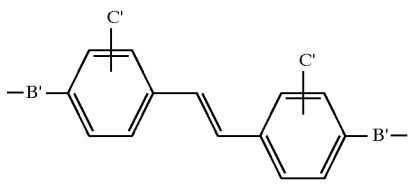

C' is —SO$_3$H;

B' is —NH;

W' is the moiety:

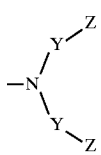

Y is —CH$_2$—;

Z=—CH$_2$OH; and

U', X, Y, n, and m are as defined in claim 1;

or a pharmaceutically acceptable salt or ester thereof.

3. A compound of claim 1 wherein A is the moiety:

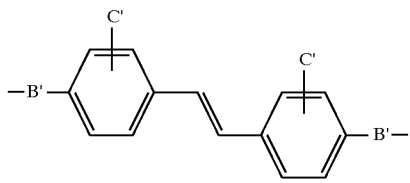

C' is —SO₃H;
B' is —NH;
W' is the moiety:

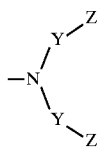

Y is —CH₂CH₂—;
Z=—CONH₂; and
U', X, Y, n, and m are as defined in claim 1;
or a pharmaceutically acceptable salt or ester thereof.

4. A compound of claim 1 wherein A is the moiety:

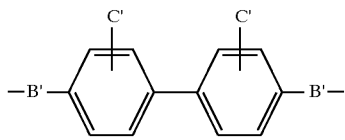

C' is —SO₃H;
B' is —NH;
W' is the moiety:

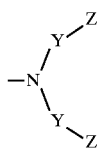

Y is —CH₂CH₂—;
Z=—CONH₂; and
U', X, Y, n, and m are as defined in claim 1;
or a pharmaceutically acceptable salt or ester thereof.

5. The compound of claim 1 in which the pharmaceutically acceptable salt thereof is a disodium salt.

6. A compound of claim 1 which is 4,4'-Bis[4,6-di[3-aminophenyl-N,N-bis(2-carbamoyl-ethyl)sulfonylimino]-1,3,5-triazin-2-ylamino]-stilbene-2,2'-disulfonic acid or a pharmaceutically acceptable salt thereof.

7. A compound of claim 1 which is 4,4'-Bis[4,6-di[3-aminophenyl-N,N-bis(2-carbamoyl-ethyl)sulfonylimino]-1,3,5-triazin-2-ylamino]-biphenyl-2,2'-disulfonic acid or a pharmaceutically acceptable salt thereof.

8. A compound of claim 1 which is 4,4'-Bis[4,6-di[3-aminophenyl-N,N-bis(2-hydroxyethyl)sulfonylimino]-1,3,5-triazin-2-ylamino]-stilbene-2,2'-disulfonic acid or a pharmaceutically acceptable salt thereof.

9. A compound of claim 1 which is 4-[4,6-Di[3-aminophenyl-N,N-bis(2-carbamoylethyl)sulfonylimino]-1,3,5-triazin-2-ylamino]-4'-[4-chloro-6-[3-aminophenyl-N,N-bis(2-carbamoylethyl)sulfonylimino]-1,3,5-triazin-2-ylamino]-stilbene-2,2'-disulphonic acid or a pharmaceutically acceptable salt thereof.

10. A compound of claim 1 which is 4,4'-Bis[4-chloro-6-[3-aminophenyl-N,N-bis(2-carbamoylethyl)sulfonylimino]-1,3,5-triazin-2-ylamino]-stilbene-2,2'-disulphonic acid or a pharmaceutically acceptable salt thereof.

11. A compound of claim 1 which is 4-[4,6-Di[3-aminophenyl-N,N-bis(2-carbamoylethyl)sulfonylimino]-1,3,5-triazin-2-ylamino]-4'-[4-[3-aminophenyl-N,N-bis(2-carbamoylethyl)sulfonylimino]-6-[3-aminophenyl-N-(2-carbamoylethyl)-N'-(3-propionic acid)]-1,3,5-triazin-2-ylamino]-stilbene-2,2'-disulphonic acid or a pharmaceutically acceptable salt thereof.

12. A compound of claim 1 which is 4-[4,6-Di[3-aminophenyl-N,N-bis(2-carbamoylethyl)sulfonylimino]-1,3,5-triazin-2-ylamino]-4'-[4-[3-aminophenyl-N,N-bis(2-carbamoylethyl)sulfonylimino]-6-[3-aminophenyl-N,N-bis(3-propionic acid)]-1,3,5-triazin-2-ylamino]-stilbene-2,2'-disulphonic acid or a pharmaceutically acceptable salt thereof.

13. A compound of claim 1 which is 4,4'-Bis[4,6-di[3-aminophenyl-N,N-bis(2-carbamoyl-ethyl)sulfonylimino]-1,3,5-triazin-2-ylamino]-bibenzyl-2,2'-disulfonic acid or a pharmaceutically acceptable salt thereof.

14. A compound of claim 1 which is 4,4'-Bis[4,6-di[4-aminophenyl-N,N-bis(2-carbamoyl-ethyl)sulfonylimino]-1,3,5-triazin-2-ylamino]-stilbene-2,2'-disulfonic acid or a pharmaceutically acceptable salt thereof.

15. A compound of claim 1 which is 4,4'-Bis[4,6-di[4-aminophenyl-N,N-bis(2-carbamoyl-ethyl)sulfonylimino]-1,3,5-triazin-2-ylamino]-biphenyl-2,2'-disulfonic acid or a pharmaceutically acceptable salt thereof.

16. A compound of claim 1 which is 4,4'-Bis[4,6-di[3-aminophenylsulphonylamido]-1,3,5-triazin-2-ylamino]-stilbene-2,2'-disulfonic acid or a pharmaceutically acceptable salt thereof.

17. A compound of claim 1 which is 4,4'-Bis[4,6-di[3-aminophenylsylphonylimido]-1,3,5-triazin-2-ylamino]-biphenyl-2,2'-disulfonic acid or a pharmaceutically acceptable salt thereof.

18. A compound of claim 1 which is 4,4'-Bis[4,6-di[3-aminophenyl-N,N-bis(2-carbamoyl-ethyl)sulfonylimino]-1,3,5-triazin-2-yloxy]-biphenyl-2,2'-disulfonic acid or a pharmaceutically acceptable salt thereof.

19. A compound of claim 1 which is 5,5'-Dimethyl-4,4'-bis[4,6-di[3-aminophenyl-N,N-bis(2-carbamoyl-ethyl)sulfonylimino]-1,3,5-triazin-2-ylamino]-biphenyl-2,2'-disulfonic acid or a pharmaceutically acceptable salt thereof.

20. A compound of claim 1 which is 4,4'-Bis[4,6-di[3-aminophenyl-N,N-bis(2-hydroxyethyl)sulfonylimino]-1,3,5-triazin-2-ylamino]-biphenyl-2,2'-disulfonic acid or a pharmaceutically acceptable salt thereof.

21. A compound of claim 1 which is 9,9-Dioxo-2,7-Bis[4,6-di[3-aminophenyl-N,N-bis(2-carbamoylethyl)sulfonylimino]-1,3,5-triazin-2-ylamino]-dibenzothiophen-3,6-disulfonic acid or a pharmaceutically acceptable salt thereof.

22. A compound of claim 1 which is 4,4'-Bis[4-chloro-6-di[4-amino-N'-[3-aminophenyl-N,N-bis(2-carbamoylethyl)sulfonylimino]-benzamide]-1,3,5-triazin-2-ylamino]-stilbene-2,2'-disulfonic acid or a pharmaceutically acceptable salt thereof.

23. A compound of claim 1 which is 4,4'-Bis[4,6-di[4-amino-N'-[3-aminophenyl-N,N-bis(2-hydroxyethyl)sulfonylimino]-benzensulfonamide]-1,3,5-triazin-2-ylamino]-stilbene-2,2'-disulfonic acid or a pharmaceutically acceptable salt thereof.

24. A compound of claim 1 which is 4,4'-Bis-(4,6-bis{3-[bis-(2-carbamoyl-ethyl)-sulfamoyl]-phenylamino}-1,3,5-triazin-2-ylamino]-biphenyl-2,2'-dicarboxylic acid, disodium salt.

25. A compound of claim 1 which is 4,4'-Bis-[[4,6-bis-[[3-[[bis-[3-(methylamino)-3-oxopropyl]amino]sulfonyl]phenyl]amino]-1,3,5-triazin-2-yl]amino][1,1'-biphenyl]-2,2'-disulfonic acid, disodium salt.

26. A compound of claim 1 which is 4,4'-Bis-(4,6-bis-{3-[bis-(2-methylcarbamoyl-ethyl)-sulfamoyl]-phenylamino}-1,3,5]triazin-2-ylamino)-biphenyl-2,2'-dicarboxylic acid, disodium salt.

27. A compound of claim 1 which is 4,4'-Bis-(4,6-bis-{3-[bis-(2-carbamoyl-ethyl)-sulfamoyl]-phenylamino}-1,3,5]triazin-2-ylamino)-biphenyl-2,2'-dicarboxylic acid dimethyl ester or a pharmaceutically acceptable salt thereof.

28. A compound of claim 1 which is 4,4'-Bis-(4,6-bis-{3-[bis-(2-hydroxy-propyl)-sulfamoyl]-phenylamino}-[1,3,5]-triazin-2-ylamino)biphenyl-2,2'-disulfonic acid, disodium salt.

29. A compound of claim 1 which is 4,4'-Bis-(4,6-bis-{3-[bis-(2-hydroxy-propyl)-sulfamoyl]-phenylamino}-[1,3,5]-triazin-2-ylamino)biphenyl-2,2'-dicarboxylic acid, disodium salt.

30. A compound of claim 1 which is 4',4-Bis-{4,6-bis-[3-(bis-carbamoylmethyl-1-sulfamoyl)-phenylamino]-[1,3,5]triazin-2-ylamino}-biphenyl-2,2'-disulfonic acid, disodium salt.

31. A compound of claim 1 which is 4',4-Bis-{4,6-bis-[3-(bis-carbamoylmethyl-1-sulfamoyl)-phenylamino]-[1,3,5]triazin-2-ylamino}-biphenyl-2,2'-dicarboxylic acid, disodium salt.

32. A compound of claim 1 which is (E)-2,2'-(1,2-Ethenediyl)bis[5-[[4.6-bis[[3-[[3,5-bis(aminocarbonyl)-1-piperedinyl]sulfonyl]phenyl]amino]-1,3,5-triazin-2-yl]amino]benzenesulfonic acid], disodium salt.

33. A compound of claim 1 which is 4',4-Bis-{4,6-bis-[3-(3,5-dicarbamoyl-piperidine-1-sulfonyl)-phenylamino]-[1,3,5]triazin-2-ylamino}-biphenyl-2,2'-disulfonic acid, disodium salt.

34. A compound of claim 1 which is 1,2',1'',1'''-[(2,2'-disulfo[1,1'-biphenyl]-4,4'-diyl)-bis[imino-1,3,5-triazine-6,2,4-triylbis(imino-3,1-phenylenesulfonyl)]tetrakis[3,5-piperidinedicarboxylic acid or a pharmaceutically acceptable salt thereof.

35. A compound of claim 1 which is 4,4'-Bis-(4,6-bis-{3-[bis-(2-hydroxyethyl)-sulfamoyl]-phenylamino}-[1,3,5]-triazin-2-ylamino)biphenyl-2,2'-dicarboxylic acid, disodium salt.

36. A compound of claim 1 which is 4,4'-Bis[4,6-di[3-aminophenyl-N,N-bis(3-hydroxypropyl)-sulfonylimino]-1,3,5-triazin-2-ylamino]-biphenyl-2,2'-disulfonic acid, disodium salt.

37. A method for treating a respiratory syncytial viral infection in a mammal, the method comprising administering to the mammal experiencing the respiratory syncytial viral infection an efficacious amount of a compound of the structure:

wherein:

A is a moiety selected from the group consisting of

C' is selected from —SO$_3$H, —OSO$_3$H, —OH, or —COOH;

B' is selected from —NH, —NR$^1$ or O;

R$^1$ is selected from H, (C$_1$–C$_6$)lower alkyl straight or branched wherein the carbon atoms may be optionally substituted with Cl, Br, F, OH or CN;

X is selected from Cl, F or the moiety

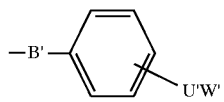

where

U' is selected from the group of —SO$_2$, —CO, —NC(O), or —NC(S);

W' is selected from the moieties:

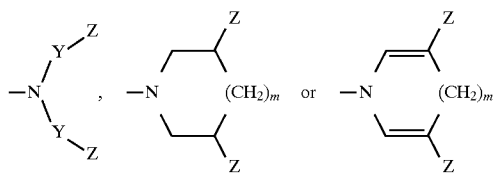

Y is —(CH$_2$)$_n$—;
n is 0 to 6;
m is 0 to 2;

Z is selected from H, CH$_3$, CF$_3$, —CH$_2$—(halogen), where halogen is Cl, Br, F or I, —CH$_2$OH, —COOH, —COO(C$_1$–C$_6$)lower alkyl straight or branched, —CONR$^2$R$^2$, CN or

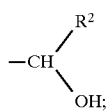

R$^2$ is independently selected from H or (C$_1$–C$_6$)lower alkyl;

or a pharmaceutically acceptable salt or ester thereof.

38. The method of claim 37 in which the efficacious amount is a dose of from about 10 mg/kg to about 500 mg/kg.

39. A pharmaceutical composition comprising a compound of the structure:

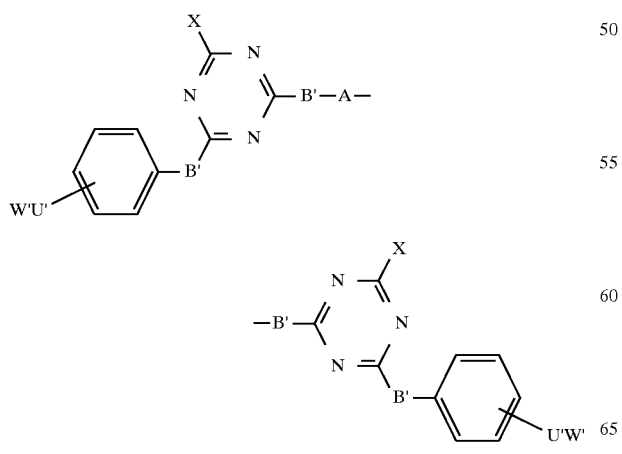

wherein:

A is a moiety selected from the group consisting of

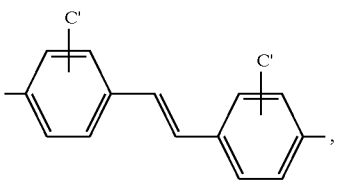

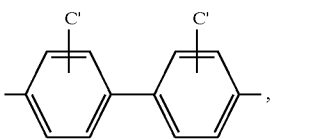

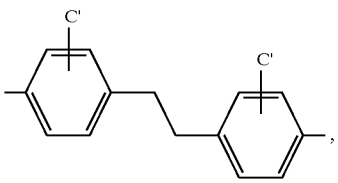

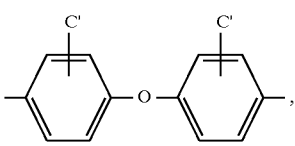

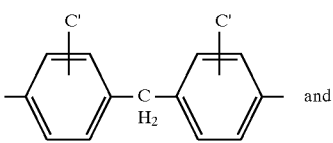

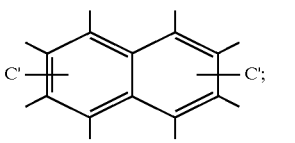

C' is selected from —SO$_3$H, —OSO$_3$H, —OH, or —COOH;

B' is selected from —NH, —NR$^1$ or O;

R$^1$ is selected from H, (C$_1$–C$_6$)lower alkyl straight or branched wherein the carbon atoms may be optionally substituted with Cl, Br, F, OH or CN;

X is selected from Cl, F or the moiety

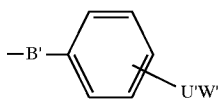

where

U' is selected from the group of —SO$_2$, —CO, —NC(O), or —NC(S);

W' is selected from the moieties:

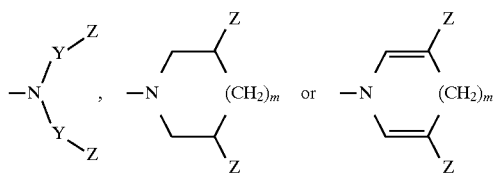

Y is —(CH$_2$)$_n$—;
n is 0 to 6;
m is 0 to 2;
Z is selected from H, CH$_3$, CF$_3$, —CH$_2$—(halogen), where halogen is Cl, Br, F or I, —CH$_2$OH, —COOH, —COO(C$_1$–C$_6$)lower alkyl straight or branched, —CONR$^2$R$^2$, CN or

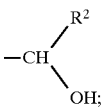

and

R$^2$ is independently selected from H or (C$_1$–C$_6$)lower alkyl;

or a pharmaceutically acceptable salt or ester thereof, and one or more pharmaceutically acceptable carriers or excipients.

* * * * *